United States Patent
Dobson et al.

(10) Patent No.: US 11,406,633 B2
(45) Date of Patent: Aug. 9, 2022

(54) DOSING SCHEDULE OF A WNT INHIBITOR AND AN ANTI-PD-1 ANTIBODY MOLECULE IN COMBINATION

(71) Applicant: Novartis AG, Basel (CH)

(72) Inventors: Jason Russell Dobson, Sharon, MA (US); Susan Moody, Cambridge, MA (US); Margaret Elise McLaughlin, Cambridge, MA (US)

( * ) Notice: Subject to any disclaimer, the term of this patent is extended or adjusted under 35 U.S.C. 154(b) by 306 days.

(21) Appl. No.: 16/482,836

(22) PCT Filed: Feb. 12, 2018

(86) PCT No.: PCT/IB2018/050846
§ 371 (c)(1),
(2) Date: Aug. 1, 2019

(87) PCT Pub. No.: WO2018/150312
PCT Pub. Date: Aug. 23, 2018

(65) Prior Publication Data
US 2019/0365746 A1 Dec. 5, 2019

Related U.S. Application Data

(60) Provisional application No. 62/616,682, filed on Jan. 12, 2018, provisional application No. 62/458,640, filed on Feb. 14, 2017.

(51) Int. Cl.
*A61K 31/497* (2006.01)
*A61P 35/00* (2006.01)
(Continued)

(52) U.S. Cl.
CPC .......... *A61K 31/497* (2013.01); *A61K 9/0053* (2013.01); *A61P 35/00* (2018.01); *C07K 16/2818* (2013.01)

(58) Field of Classification Search
None
See application file for complete search history.

(56) References Cited

U.S. PATENT DOCUMENTS

2016/0303137 A1   10/2016   Radovich

FOREIGN PATENT DOCUMENTS

WO      2016196218      * 12/2016
WO      2016196218 A1    12/2016

OTHER PUBLICATIONS

Clinical Trials, https://clinicaltrials.gov/ct2/show/NCT01351103[retrieved, 2011, from internet Aug. 11, 2021 (Year: 2011).*

(Continued)

*Primary Examiner* — Karl J Puttlitz
(74) *Attorney, Agent, or Firm* — Michelle Han

(57) ABSTRACT

The present disclosure relates to the field of pharmacy, particularly to a Wnt inhibitor and a PD-1 inhibitor for use in the treatment of cancer. Specifically, the disclosure relates to a pharmaceutical combination comprising a Wnt inhibitor, or a pharmaceutically acceptable salt thereof, and a PD-1 inhibitor, or a pharmaceutically acceptable salt thereof, for use in the treatment of cancer, to a method for the treatment of cancer that involves administering the combination and to the use of the combination for the manufacture of a medicament for the treatment of cancer.

24 Claims, 8 Drawing Sheets

Specification includes a Sequence Listing.

(51) Int. Cl.
 *A61K 9/00* (2006.01)
 *C07K 16/28* (2006.01)

(56) References Cited

OTHER PUBLICATIONS

Tol et al., N Engl J Med 2009; 360:563-572 (Year: 2009).*
Janku et al., Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C45 (Year: 2015).*
Naing et al., Journal of Clinical Oncology, Issue: vol. 34(15) Supplement, May 20, 2016, p. 3060 (Year: 2016).*
Anonymous: "A study of LGK974 in patients with malignancies dependent on wnt ligands", Clinical Trials, May 10, 2011, XP002780915,Retrieved from the Internet:URL:https://clinicaltrials.gov/ct2/show/NCT01351103?LGK974&rank=1 [retrieved on May 9, 2018].
Janku et al., "Abstract C45: Phase I study of WNT974, a first in class porcupine inhibitor, in advanced solid tumors", Molecular Cancer Therapeutics, vol. 14, No. 12 suppl 2, Dec. 2015.
Naing et al., "A first in human phase I study of the anti-PD-1 antibody PDR001 in patients with advanced solid tumors", Journal of Clinical Oncology, vol. 34, No. 15 suppl, 3060, May 20, 2016.
Liu et al., "Targeting Wnt-driven cancer through the inhibition of Porcupine by LGK974", Proceedings of the National Academy of Sciences, vol. 110, No. 50, Nov. 25, 2013, pp. 20224-20229.
International Statistical Classification of Diseases and Related Health Problems. 10th Revision (ICD-10). vol. 1 (Part 1). Geneva: World Health Organization, 1995. 698 pages.
Mashkovskiy M.D., Lekarstvennye sredstva (Medicaments).—16th edition, revised and updated.—M.: Novaya volna, 2012. 1216 pages, english translation.
Jakubke H.D. et al., Amino Acids, Peptides and Proteins. Cand. Chem. Sci., N.P. Zapevalova and Cand. Chem. Sci., E.E. Maksimova, edited by M.: Mir, 1985. 456 pages, english translation.

* cited by examiner

Genes In The T-Cell Signature: CD2, CD247, CD3D, CD3E, CD3EAP, CD3G, CD48, CD53, CD8A, CD8B, CXCR6, GZMK, LY9, SH2D1A, SLAMF6, TARP, TCF7, CD337.

DOSING SCHEDULE OF A WNT INHIBITOR AND AN ANTI-PD-1 ANTIBODY MOLECULE IN COMBINATION

FIELD OF THE DISCLOSURE

The present disclosure relates to the field of pharmacy, particularly to a Wnt inhibitor and an anti-PD-1 antibody molecule for use in the treatment of cancer. Specifically, the disclosure relates to a pharmaceutical combination comprising a Wnt inhibitor, or a pharmaceutically acceptable salt thereof, and an anti-PD-1 antibody molecule, or a pharmaceutically acceptable salt thereof, for use in the treatment of cancer; to a method for the treatment of cancer that involves administering the combination; and to the use of the combination for the manufacture of a medicament for the treatment of cancer.

BACKGROUND OF THE DISCLOSURE

The Wnt (Wingless) family is a group of highly conserved secreted proteins that regulate cell-to-cell interactions during embryogenesis and is implicated in carcinogenesis, aging, and fibrosis. The Wnt gene was identified as an oncogene in murine mammary tumors 30 years ago and confirmed to be a key oncogenic pathway in many studies. The Wnt gene family encodes a large class of secreted proteins related to the Int1/Wnt1 proto-oncogene and *Drosophila* wingless ("Wg"), a *Drosophila* Wnt1 homologue (Cadigan et al. *Genes & Development* 1997, 11, 3286).

The Programmed Death 1 (PD-1) protein is an inhibitory member of the extended CD28/CTLA4 family of T-cell regulators (Okazaki et al. *Curr. Opin. Immunol.* 2002, 14, 391779; Bennett et al. *J. Immunol.* 2003, 170, 711). Ligands of the CD28 receptor include a group of related B7 molecules, also known as the "B7 Superfamily" (Coyle et al. *Nature Immunol.* 2001, 2(3), 203; Sharpe et al. *Nature Rev. Immunol.* 2002, 2, 116; Collins et al. *Genome Biol.* 2005, 6, 223.1; Korman et al. *Adv. Immunol.* 2007, 90, 297). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins et al. *Genome Biol.* 2005, 6, 223.1). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

PD-L1 is abundant in a variety of human cancers (Dong et al. *Nat. Med.* 2002, 8, 787). PD-1 is known as an immune-inhibitory protein that negatively regulates TCR signals (Ishida et al. *EMBO J.* 1992, 11, 3887; Blank et a. *Immunol. Immunother.* 2006, 56(5), 739). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. *J. Mol. Med.* 2003, 81, 281; Blank et al. *Cancer Immunol. Immunother.* 2005, 54, 307; Konishi et al. *Clin. Cancer Res.* 2004, 10, 5094). Immune suppression can be reversed by inhibiting the local interaction of PD-1 with PD-L1 or PD-L2; the effect is additive when the interaction of PD-1 with PD-L2 is blocked as well (Iwai et al. *Proc. Not. Acad. Sci. USA* 2002, 99:12293-7; Brown et al. *J. Immunol.* 2003, 170, 1257).

Several lines of evidence suggest that Wnt pathway signaling may be important in a variety of cancers. Mutations in components of the canonical Wnt pathway, such as APC and β-catenin, might play important roles in the pathogenesis of some malignancies. Recent molecular analysis of human metastatic melanoma samples revealed a correlation between activation of the WNT/b-catenin signaling pathway and the absence of a T-cell gene expression signature (Spranger et al. *Nature* 2015, 523, 231).

SUMMARY OF THE DISCLOSURE

Given the importance of immune checkpoint pathways in regulating an immune response in cancer therapy, the need exists to develop novel combination therapies that activate the immune system or overcome the resistance to immunotherapies.

The invention addresses this need by providing a pharmaceutical combination as defined herein.

The first aspect of the present disclosure is a pharmaceutical combination comprising a Wnt inhibitor of formula (i), 2-(2',3-dimethyl-[2,4'-bipyridin]-5-yl)-N-(5-(pyrazin-2-yl)pyridin-2-yl)acetamide [Compound of Formula (I)], or a pharmaceutically acceptable salt thereof, Formula (I)

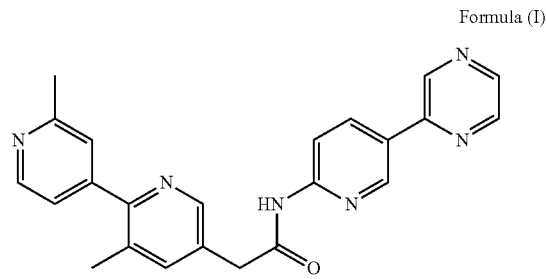 [SMILES: Cc1cc(-c2ncc(CC(=O)Nc3ccc(-c4cnccn4)cn3)cc2C)ccn1]

and (ii) an anti-PD-1 antibody molecule or a pharmaceutically acceptable salt thereof, for use in the treatment of cancer, wherein (i) is administered daily on days 1 to 15 of each cycle for up to 4 cycles and (ii) is administered at least once per cycle.

Another aspect of the present disclosure provides the use of a wnt inhibitor of formula (i), 2-(2',3-dimethyl-[2,4'-bipyridin]-5-yl)-N-(5-(pyrazin-2-yl)pyridin-2-yl)acetamide, or a pharmaceutically acceptable salt thereof, in combination with an anti-PD-1 antibody molecule (ii), or a pharmaceutically acceptable salt, for the manufacture of a medicament for the treatment of cancer, wherein (i) and (ii) are administered as define herein, preferably wherein (i) is administered daily on days 1 to 15 of each cycle for up to 4 cycles and (ii) is administered at least once per cycle.

A yet another aspect of the present disclosure provides a method for the treatment of cancer, said method comprising administering an effective amount of the (i) and (ii) to a patient in need thereof, wherein (i) is administered daily on days 1 to 15 of each cycle for up to 4 cycles and (ii) is administered at least once per cycle.

DETAILED DESCRIPTION OF THE DISCLOSURE

Figure 1A:
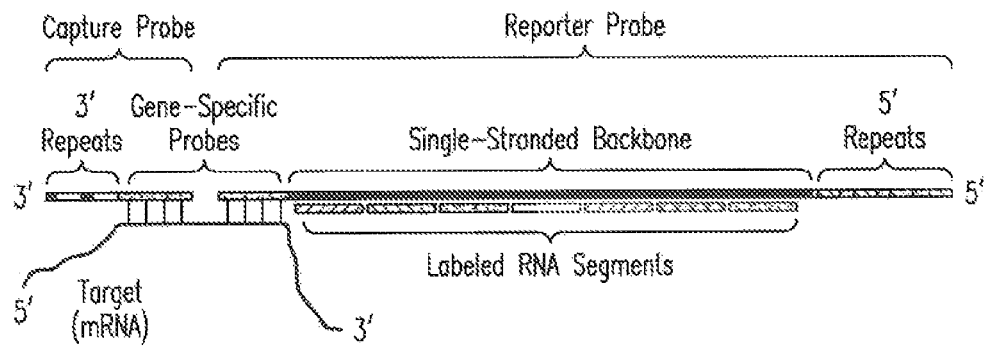
FIG. 1 presents the NanoString measured gene expression of RNA samples isolated from tumor biopsies after 15 days exposure.
Figure 1B:
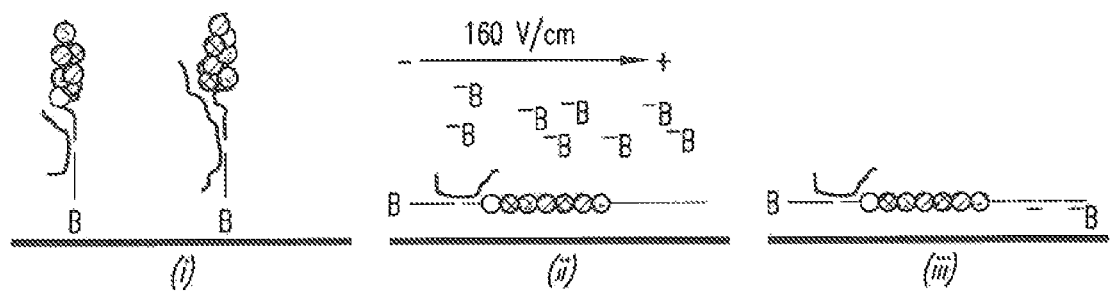
Figure 1C:
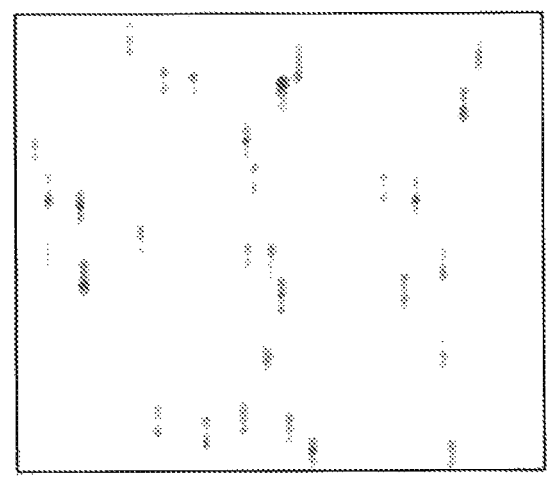

Recently, the secreted glycoproteins R-spondins 1-4 (RSPO1-4) have emerged as important activators of canonical Wnt signaling. RSPOs bind to leucine-rich repeat-containing G-protein-coupled receptors (LGR4-6) and the transmembrane E3 ubiquitin ligases RING finger 43/zinc and RING finger 3 (RNF43/ZNRF3), forming a ternary complex (Chen et al. *Genes Dev*; 2013, 27, 1345). RNF43/ZNRF3 antagonize Wnt signaling by promoting the turnover of Fz and LRP6 (Hao et al. *Nature* 2012, 485 (7397), 195-200; Koo et al. *Nature*, 2012, 488 (7413), 665). Binding of RSPO induces the endocytosis of RNF43/ZNRF3, thereby increasing levels of membrane-bound Fz and LRP6 and enhancing Wnt ligand-mediated signaling. In order to activate signaling within target cells, Wnt proteins must be properly secreted and transported across the extracellular space. Porcupine is a membrane-bound-O-acyltransferase (MBOAT) that adds palmitoyl groups to Wnt proteins (Takada et al. *Dev. Cell* 2006, 11, 791). Mutations in components of the canonical Wnt pathway such as APC and β-catenin play important roles in the pathogenesis of some malignancies and those genetic lesions affect upstream Wnt pathway regulation. The inhibition of the Wnt pathway signaling was recently associated with several drawbacks such as side effects and dose limiting toxicities. Such drawbacks were limiting the anti-tumor efficacy of Wnt inhibitors. Separately, activation of the Wnt pathway was linked to resistance to immunotherapy and offers a mechanism by which tumors can evade immune detection and decrease clinical benefit to check-point inhibitors (Spranger et al. *Nature* 2015, 523, 231). For example, the Wnt inhibitor of the present disclosure, namely 2-(2',3-dimethyl-[2,4'-bipyridin]-5-yl)-N-(5-(pyrazin-2-yl)pyridin-2-yl)acetamide was tested and the levels of pLRP6 and AXIN2qPCR were analyzed in biopsies of skin and tumors. The levels of pLRP6 and AXIN2 were inhibited in post-treatment skin sample biopsies with 2-(2',3-dimethyl-[2,4'-bipyridin]-5-yl)-N-(5-(pyrazin-2-yl)pyridin-2-yl)acetamide, or a pharmaceutically acceptable salt thereof, indicating inhibition of the Wnt pathway. Unfortunately, in other studies 2-(2',3-dimethyl-[2,4'-bipyridin]-5-yl)-N-(5-(pyrazin-2-yl)pyridin-2-yl)acetamide, or a pharmaceutically acceptable salt thereof, alone as a single agent showed an increased cytotoxic gene signature and a lack of tumor efficacy. In addition, animal studies showed a decrease in trabeculae in rat studies; toxicities in gastrointestinal (GI) tract, bones and teeth in rat and dog models; and secondary effects affecting the bone marrow in rats and kidneys in dogs.

It has been discovered that treatment of patients with the Wnt inhibitor (i) alone resulted in changes in immune signatures in tumors and that 8-15 days of treatment with the single agent Wnt inhibitor (i) was sufficient to result in these changes. These findings led to conclude that intermittent dosing of a Wnt inhibitor (i) with an anti-PD-1 antibody molecule (ii), or a pharmaceutically acceptable salt thereof, can sensitize dendritic and T-cells and thus be sufficient to enhance the effects of PD-1 inhibition, while mitigating some of the toxicities of chronic Wnt administration, particularly to the bone.

The Wnt signaling pathway is required for development and survival of osteoblasts (involved in bone formation) and negatively regulates osteoclasts (involved in bone resorption). Linked to that, Wnt inhibitors were found to cause bone resorption and bone thinning. In a clinical study of the Wnt inhibitor, some patients experienced bone fractures, which may be related to the effects of the Wnt pathway inhibition on osteoblasts and osteoclasts. Therefore, administering the Wnt inhibitor (i), e.g. 2-(2',3-dimethyl-[2,4'-bipyridin]-5-yl)-N-(5-(pyrazin-2-yl)pyridin-2-yl)acetamide, or a pharmaceutically acceptable salt thereof, for a shorter period such as daily only on days 1 to 15 of up to 4 therapeutic cycles can reduce the risk of the Wnt inhibitor causing clinically relevant changes to the bone. In addition, the short intermittent dosing of Wnt inhibitor was sufficient to result in upregulation of the activated dendritic cells signature. This is relevant because this subtype of dendritic cell is important for recruiting and activating T cells for an anti-tumoral response. Inhibition of the Wnt signaling in cancer treatment improves the response rate to PD-1 inhibition through release of inhibition of dendritic cells and T-cell activation. Overall, the combination of the Wnt inhibitor (i) and an anti-PD-1 antibody molecule, wherein Wnt inhibitor is administered only at the beginning of the treatment cycle for, e.g. 8 or 15 days, can show mutually coordinated effect of both compounds and offer better efficacy and much reduced safety profile compared to, for example, use of the Wnt inhibitor (i) alone.

According to the present disclosure, the Wnt inhibitor is a compound that targets, decreases or inhibits the activity of the Wnt signaling in a cell. For example, the Wnt inhibitor can also be a porcupine inhibitor. The Wnt inhibitor (i) is a compound disclosed in WO2010/101849. The Wnt inhibitor to be combined with the anti-PD-1 antibody molecule, or a pharmaceutical salt thereof, is 2-(2',3-dimethyl-2,4'-bipyridin-5-yl)-N-(5-(pyrazin-2-yl)pyridin-2-yl)acetamide, or a pharmaceutically acceptable salt thereof, of formula (I)

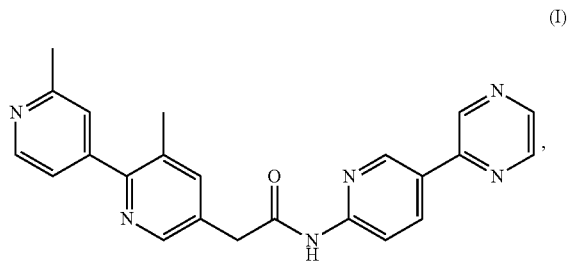 [SMILES: Cc1cc(-c2ncc(CC(=O)Nc3ccc(-c4cnccn4)cn3)cc2C)ccn1]

(I)

as disclosed in WO2010/101849 (compound 86, example 10).

Therefore the present disclosure provides a pharmaceutical combination comprising (i) 2-(2',3-dimethyl-[2,4'-bipyridin]-5-yl)-N-(5-(pyrazin-2-yl)pyridin-2-yl)acetamide, or a pharmaceutically acceptable salt thereof, and (ii) an anti-PD-1 antibody molecule or a pharmaceutically acceptable salt thereof, for use in the treatment of cancer, wherein the compound of formula (i), namely 2-(2',3-dimethyl-[2,4'- bipyridin]-5-yl)-N-(5-(pyrazin-2-yl)pyridin-2-yl)acetamide, or a pharmaceutically acceptable salt thereof, is administered daily on days 1 to 15 of each cycle for up to 4 cycles and anti-PD-1 antibody molecule (ii) as described herein is administered at least once per cycle. The Wnt inhibitor can be administered for 4 cycles.

In the present disclosure the term "pharmaceutical combination" refers to a non-fixed combination. The term "non-fixed combination" means that the active ingredients, e.g. compound of formula (i), namely 2-(2',3-dimethyl-[2,4'-bipyridin]-5-yl)-N-(5-(pyrazin-2-yl)pyridin-2-yl)acetamide, or a pharmaceutically acceptable salt thereof and an anti-PD-1 antibody molecule, or a pharmaceutically acceptable salt form, are both administered to a patient as separate entities either simultaneously or sequentially with no specific time limits, wherein such administration provides therapeutically effective levels of the two compounds in the body of the patient.

The terms "a combination" or "in combination with," it is not intended to imply that the therapy or the therapeutic agents must be administered at the same time and/or formulated for delivery together, although these methods of delivery are within the scope described herein. The therapeutic agents in the combination can be administered concurrently with, prior to, or subsequent to, one or more other additional therapies or therapeutic agents. The therapeutic agents or therapeutic protocol can be administered in any order. In general, each agent will be administered at a dose and/or on a time schedule determined for that agent. In will further be appreciated that the additional therapeutic agent utilized in this combination may be administered together or separately in different compositions. In general, it is expected that additional therapeutic agents utilized in combination be utilized at levels that do not exceed the levels at which they are utilized individually. In some embodiments, the levels utilized in combination will be lower than those utilized individually.

The anti-PD-1 antibody molecule, or a pharmaceutically acceptable salts thereof, that can be used in combination with Wnt inhibitors of the present disclosure, is any anti-PD-1 antibody as disclosed herein. For example, the anti-PD-1 antibody molecule can comprise at least one antigen-binding region, e.g., a variable region or an antigen-binding fragment thereof, from an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD1 antibody molecule is preferably selected from nivolumab (Opdivo), pembrolizumab (Keytruda), pidilizumab, PDR-001, or a pharmaceutical salt thereof. Most preferably the anti-PD-1 antibody molecule is PDR-001, or a pharmaceutical salt thereof. The anti-PD-1 antibody molecule designated as PDR-001 was described in PCT/CN2016/099494. More particularly the PDR-001 inhibitor, or a pharmaceutically acceptable salt thereof, comprises a heavy chain variable region (VH) comprising a HCDR1, a HCDR2 and a HCDR3 amino acid sequence of BAP049-Clone-E and a light chain variable region (VL) comprising a LCDR1, a LCDR2 and a LCDR3 amino acid sequence of BAP049-Clone-E as described in Table 1.

The anti-PD-1 antibody molecule, or a pharmaceutically acceptable salt thereof, of the present disclosure comprises, for example, at least one, two, three or four variable regions from an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

The anti-PD-1 antibody molecule, or a pharmaceutically acceptable salt thereof, of the present disclosure comprises, for example, at least one or two heavy chain variable regions from an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

The anti-PD-1 antibody molecule, or a pharmaceutically acceptable salt thereof, of the present disclosure comprises, for example, at least one or two light chain variable regions from an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

The anti-PD-1 antibody molecule, or a pharmaceutically acceptable salt thereof, of the present disclosure includes, for example, a heavy chain constant region for an IgG4, e.g., a human IgG4. The human IgG4 includes a substitution at position 228 according to EU numbering (e.g., a Ser to Pro substitution). The anti-PD-1 antibody molecule includes a heavy chain constant region for an IgG1, e.g., a human IgG1. The human IgG1 includes a substitution at position 297 according to EU numbering (e.g., an Asn to Ala substitution). The human IgG1 may also include a substitution at position 265 according to EU numbering, a substitution at position 329 according to EU numbering, or both (e.g., an Asp to Ala substitution at position 265 and/or a Pro to Ala substitution at position 329). The human IgG1 also includes a substitution at position 234 according to EU numbering, a substitution at position 235 according to EU numbering, or both (e.g., a Leu to Ala substitution at position 234 and/or a Leu to Ala substitution at position 235). The heavy chain constant region comprises an amino sequence set forth in Table 3, or a sequence substantially identical (e.g., at least 80%, 85%, 90%, 92%, 95%, 97%, 98%, 99% or higher identical) thereto.

The anti-PD-1 antibody molecule, or a pharmaceutically acceptable salt thereof, according to the present disclosure includes, for example, a kappa light chain constant region, e.g., a human kappa light chain constant region. The light chain constant region comprises an amino sequence set forth in Table 3, or a sequence substantially identical (e.g., at least 80%, 85%, 90%, 92%, 95%, 97%, 98%, 99% or higher identical) thereto.

The anti-PD-1 antibody molecule, or a pharmaceutically acceptable salt thereof, according to the present disclosure also includes, for example, a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. The human IgG4 includes a substitution at position 228 according to EU numbering (e.g., a Ser to Pro substitution). The anti-PD-1 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. The human IgG1 may also include a substitution at position 297 according to EU numbering (e.g., an Asn to Ala substitution). The human IgG1 includes a substitution at position 265 according to EU numbering, a substitution at position 329 according to EU numbering, or both (e.g., an Asp to Ala substitution at position 265 and/or a Pro to Ala substitution at position 329). The human IgG1 includes a substitution at position 234 according to EU numbering, a substitution at position 235 according to EU numbering, or both (e.g., a Leu to Ala substitution at position 234 and/or a Leu to Ala substitution at position 235).

The anti-PD-1 antibody molecule, or a pharmaceutically acceptable salt thereof, of the present disclosure also includes, for example, a heavy chain variable domain and a constant region, a light chain variable domain and a constant region, or both, comprising the amino acid sequence of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4; or a sequence substantially identical thereto.

Theanti-PD-1 antibody molecule, or a pharmaceutically acceptable salt thereof, according to the present disclosure includes at least one, two, or three complementarity determining regions (CDRs) from a heavy chain variable region of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

The anti-PD-1 antibody molecule, or a pharmaceutically acceptable salt thereof, according to the present disclosure includes, for example, at least one, two, or three CDRs (or collectively all of the CDRs) from a heavy chain variable region comprising an amino acid sequence shown in Table 1, or encoded by a nucleotide sequence shown in Table 1. One or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

The anti-PD-1 antibody molecule, or a pharmaceutically acceptable salt thereof, according to the present disclosure includes, for example, at least one, two, or three CDRs from a light chain variable region of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequence.

The anti-PD-1 antibody molecule, or a pharmaceutically acceptable salt thereof, includes, for example, at least one, two, or three CDRs (or collectively all of the CDRs) from a heavy chain variable region comprising an amino acid sequence shown in Table 1, or encoded by a nucleotide sequence shown in Table 1. One or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

The anti-PD-1 antibody molecule, or a pharmaceutically acceptable salt thereof, includes, for example, at least one, two, or three CDRs from a light chain variable region of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequence.

The anti-PD-1 antibody molecule, or a pharmaceutically acceptable salt thereof, includes, for example, at least one, two, or three CDRs (or collectively all of the CDRs) from a light chain variable region comprising an amino acid sequence shown in Table 1, or encoded by a nucleotide sequence shown in Table 1. One or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-1 antibody molecule, or a pharmaceutically acceptable salt thereof, includes a substitution in a light chain CDR, e.g., one or more substitutions in a CDR1, CDR2 and/or CDR3 of the light chain. The anti-PD-1 antibody molecule, or a pharmaceutically acceptable salt thereof, includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 54 or 70 for a modified sequence).

The anti-PD-1 antibody molecule, or a pharmaceutically acceptable salt thereof, according to the present disclosure includes, for example, at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

The anti-PD-1 antibody molecule, or a pharmaceutically acceptable salt thereof, of the present disclosure includes, for example, all six CDRs from an antibody described herein, e.g., an antibody chosen from any of BAP049-Clone-B or BAP049-Clone-E; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). The anti-PD-1 antibody molecule, or a pharmaceutically acceptable salt thereof, may also include any CDR described herein. The anti-PD-1 antibody molecule, or a pharmaceutically acceptable salt thereof, includes a substitution in a light chain CDR, e.g., one or more substitutions in a CDR1, CDR2 and/or CDR3 of the light chain. The anti-PD-1 antibody molecule, or a pharmaceutically acceptable salt thereof, according to the present disclosure, includes a substitution in the light chain CDR3 at position 102 of the light variable region, e.g., a substitution of a cysteine to tyrosine, or a cysteine to serine residue, at position 102 of the light variable region according to Table 1.

The anti-PD-1 antibody molecule, or a pharmaceutically acceptable salt thereof, of the present disclosure, includes at least one, two, or three CDRs according to Kabat et al. (e.g., at least one, two, or three CDRs according to the Kabat definition as set out in Table 1) from a heavy chain variable region of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

The anti-PD-1 antibody molecule, or a pharmaceutically acceptable salt thereof, of the present invention, includes, for example, at least one, two, or three CDRs according to Kabat et al. (e.g., at least one, two, or three CDRs according to the Kabat definition as set out in Table 1) from a light chain variable region of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

The anti-PD-1 antibody molecule, or a pharmaceutically acceptable salt thereof, according to the present disclosure, includes, for example, at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five or six CDRs according to Kabat et al. shown in Table 1.

The anti-PD-1 antibody molecule, or a pharmaceutically acceptable salt thereof, of the present disclosure, includes all six CDRs according to Kabat et al. (e.g., all six CDRs according to the Kabat definition as set out in Table 1) from the heavy and light chain variable regions of an antibody described herein, e.g., an antibody chosen from any of BAP049-Clone-B or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. The anti-PD-1 antibody molecule, or a pharmaceutically acceptable salt thereof, according to the present disclosure, may include any CDR described herein.

The anti-PD-1 antibody molecule, or a pharmaceutically acceptable salt thereof, according to the present disclosure, includes, for example at least one, two, or three Chothia hypervariable loops (e.g., at least one, two, or three hypervariable loops according to the Chothia definition as set out in Table 1) from a heavy chain variable region of an antibody described herein, e.g., an antibody chosen from any of BAP049-Clone-B or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

The anti-PD-1 antibody molecule, or a pharmaceutically acceptable salt thereof, according to the present disclosure, includes, for example, at least one, two, or three Chothia hypervariable loops (e.g., at least one, two, or three hypervariable loops according to the Chothia definition as set out in Table 1) of a light chain variable region of an antibody described herein, e.g., an antibody chosen from any of BAP049-Clone-B or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

The anti-PD-1 antibody molecule, or a pharmaceutically acceptable salt thereof, according to the present disclosure, includes, for example, at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP049-Clone-B or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table 1.

The anti-PD-1 antibody molecule, or a pharmaceutically acceptable salt thereof, according to the present disclosure, includes, for example, all six hypervariable loops (e.g., all six hypervariable loops according to the Chothia definition as set out in Table 1) of an antibody described herein, e.g., an antibody chosen from any of BAP049-Clone-B or BAP049-Clone-E, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table 1. The anti-PD-1 antibody molecule, or a pharmaceutically acceptable salt thereof, according to the present disclosure may include any hypervariable loop described herein.

The anti-PD-1 antibody molecule, or a pharmaceutically acceptable salt thereof, according to the present disclosure, includes, for example, at least one, two, or three hypervariable loops that have the same canonical structures as the corresponding hypervariable loop of an antibody described herein, e.g., an antibody chosen from any of BAP049-Clone-B or BAP049-Clone-E, e.g., the same canonical structures as at least loop 1 and/or loop 2 of the heavy and/or light chain variable domains of an antibody described herein. (See, e.g., Chothia et al. *J. Mol. Biol.* 1992, 227, 799; Tomlinson et al. *J. Mol. Biol.* 1992, 227:776-798 for descriptions of hypervariable loop canonical structures). These structures can be determined by inspection of the tables described in these references.

The anti-PD-1 antibody molecule, or a pharmaceutically acceptable salt thereof, according to the present disclosure, may also include, for example, a combination of CDRs or hypervariable loops defined according to the Kabat et al. and Chothia et al. as described herein in Table 1.

The anti-PD-1 antibody molecule, or a pharmaceutically acceptable salt thereof, according to the present disclosure, includes, for example, at least one, two or three CDRs or hypervariable loops from a heavy chain variable region of an antibody described herein, e.g., an antibody chosen from any of BAP049-Clone-B or BAP049-Clone-E, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-PD-1 antibody molecule, or a pharmaceutically acceptable salt thereof, according to the present disclosure, can include VH CDR1 according to Kabat et al. or VH hypervariable loop 1 according to Chothia et al., or a combination thereof, e.g., as shown in Table 1.

The combination of Kabat and Chothia CDR of VH CDR1 comprises the amino acid sequence GYTFTTYWMH (SEQ ID NO: 224), or an amino acid sequence substantially identical thereto (e.g., having at least one amino acid alteration, but not more than two, three or four alterations (e.g., substitutions, deletions, or insertions, e.g., conservative substitutions). The anti-PD-1 antibody molecule can further include, e.g., VH CDRs 2-3 according to Kabat et al. and VL CDRs 1-3 according to Kabat et al., e.g., as shown in Table 1. Accordingly, the framework regions (FW) are defined based on a combination of CDRs defined according to Kabat et al. and hypervariable loops defined according to Chothia et al. For example, the anti-PD-1 antibody molecule can include VH FW1 defined based on VH hypervariable loop 1 according to Chothia et al. and VH FW2 defined based on VH CDRs 1-2 according to Kabat et al., e.g., as shown in Table 1. The anti-PD-1 antibody molecule can further include, e.g., VH FWs 3-4 defined based on VH CDRs 2-3 according to Kabat et al. and VL FWs 1-4 defined based on VL CDRs 1-3 according to Kabat et al.

The anti-PD-1 antibody molecule, or a pharmaceutically acceptable salt thereof, according to the present disclosure, includes at least one, two or three CDRs from a light chain variable region of an antibody described herein, e.g., an antibody chosen from any of BAP049-Clone-B or BAP049-Clone-E, according to the Kabat and Chothia definitions (e.g., at least one, two, or three CDRs according to the Kabat and Chothia definitions as set out in Table 1).

The anti-PD-1 antibody molecule, or a pharmaceutically acceptable salt thereof, according to the present disclosure, includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

The anti-PD-1 antibody molecule, or a pharmaceutically acceptable salt thereof, according to the present disclosure, comprises a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33.

The anti-PD-1 antibody molecule, or a pharmaceutically acceptable salt thereof, according to the present disclosure, can comprise, for example, a heavy chain variable domain comprising the amino acid sequence of SEQ ID NO: 38 and a light chain variable domain comprising the amino acid sequence of SEQ ID NO: 70.

The anti-PD-1 antibody molecule, or a pharmaceutically acceptable salt thereof, according to the present disclosure, can comprise, for example, a heavy chain comprising the amino acid sequence of SEQ ID NO: 91 and a light chain comprising the amino acid sequence of SEQ ID NO: 72.

The anti-PD-1 antibody molecule, or a pharmaceutically acceptable salt thereof, according to the present disclosure, comprises a heavy chain variable region (VH) comprising a HCDR1, a HCDR2 and a HCDR3 amino acid sequence of BAP049-Clone-B or BAP049-Clone-E as described in Table 1 and a light chain variable region (VL) comprising a LCDR1, a LCDR2 and a LCDR3 amino acid sequence of BAP049-Clone-B or BAP049-Clone-E as described in Table 1.

The anti-PD-1 antibody molecule, or a pharmaceutically acceptable salt thereof, according to the present disclosure, comprises a heavy chain variable region (VH) comprising a HCDR1, a HCDR2 and a HCDR3 amino acid sequence of BAP049-Clone-E as described in Table 1 and a light chain variable region (VL) comprising a LCDR1, a LCDR2 and a LCDR3 amino acid sequence of BAP049-Clone-E as described in Table 1.

It is understood that the anti-PD-1 antibody molecule, or the anti-PD-1 antibody molecule, of the present disclosure may have additional conservative or non-essential amino acid substitutions, which do not have a substantial effect on their functions.

The term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). An antibody molecule comprises a full length antibody, or a full length immunoglobulin chain, or an antigen binding or functional fragment of a full length antibody, or a full length immunoglobulin chain. An antibody molecule can also be a multi-specific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope.

The term "Pharmaceutically acceptable salts" can be formed, for example, as acid addition salts, preferably with organic or inorganic acids. Suitable inorganic acids are, for example, halogen acids, such as hydrochloric acid. Suitable organic acids are, e.g., carboxylic acids or sulfonic acids, such as fumaric acid or methanesulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. Any reference to the free compound herein is to be understood as referring also to the corresponding salt, as appropriate and expedient. The salts of the inhibitors, as described herein, are preferably pharmaceutically acceptable salts; suitable counter-ions forming pharmaceutically acceptable salts are known in the field.

The term "pharmaceutically acceptable" refers to those compounds, materials, compositions, and/or dosage forms which are suitable for use in contact with the tissues of human beings and animals without excessive toxicity, irritation, allergic response, or other problem or complication, commensurate with a reasonable benefit/risk ratio.

The term "inhibition" or "inhibitor" includes a reduction in a certain parameter, e.g., an activity, of a given molecule, e.g., an immune checkpoint inhibitor, such as the anti-PD-1 antibody molecule. For example, inhibition of an activity, e.g., a PD-1 or PD-L1 activity, of at least 5%, 10%, 20%, 30%, 40% or more is included by this term. Thus, inhibition need not be 100%.

The term "cancer" refers to a disease characterized by the rapid and uncontrolled growth of aberrant cell proliferation. Cancer cells can spread locally or through the bloodstream and lymphatic system to other parts of the body. Examples of various cancers are, but are not limited to, leukemia, prostate cancer, renal cancer, liver cancer, brain cancer, lymphoma, ovarian cancer, lung cancer, cervical cancer, skin cancer, breast cancer, head and neck squamous cell carcinoma (HNSCC), pancreatic cancer, gastrointestinal cancer, colorectal cancer, triple-negative breast cancer (TNBC), squamous cell cancer of the lung, squamous cell cancer of the esophagus, squamous cell cancer of the cervix, or melanoma. According to the disclosure the particularly amenable disease conditions to be treated with the aforementioned combination are triple-negative breast cancer (TNBC), pancreatic cancer, squamous cell cancer of the lung, squamous cell cancer of the esophagus, squamous cell cancer of the cervix, or melanoma.

The terms "tumor" and "cancer" are used interchangeably herein, e.g., both terms encompass solid and liquid, e.g., diffuse or circulating tumors. In one embodiment, the term "cancer" or "tumor" includes malignant cancers and tumors, as well as advanced cancers and tumors.

The term "treatment" comprises, for example, the therapeutic administration of the combination of a Wnt inhibitor, or a pharmaceutically acceptable salt thereof, and an anti-PD-1 antibody molecule, or a pharmaceutically acceptable salt thereof, as described herein to a warm-blooded animal, in particular a human being, in need of such treatment with the aim to cure the disease or to have an effect on disease regression or on the delay of progression of a disease. The terms "treat", "treating" or "treatment" of any disease or disorder refers to ameliorating the disease or disorder (e.g. slowing or arresting or reducing the development of the disease or at least one of the clinical symptoms thereof), to preventing or delaying the onset or development or progression of the disease or disorder.

A Wnt inhibitor, (i) 2-(2',3-dimethyl-[2,4'-bipyridin]-5-yl)-N-(5-(pyrazin-2-yl)pyridin-2-yl)acetamide, or a pharmaceutically acceptable salt thereof can be administered daily on days 1 to 15 of each cycle or on days 1 to 8 of each cycle. The Wnt inhibitor, (i) 2-(2',3-dimethyl-[2,4'-bipyridin]-5-yl)-N-(5-(pyrazin-2-yl)pyridin-2-yl)acetamide can be administered up to 4 cycles. The Wnt inhibitor (i) can be administered during 4 cycles. It can also be administered in the first cycle only. Preferably, the Wnt inhibitor (i) is administered during days 1 to 15 of each cycle for up to 4 cycles. Most preferably, the Wnt inhibitor (i) is administered daily on days 1 to 8 of each cycle for up to 4 cycles. The present invention also provides that (i) 2-(2',3-dimethyl-[2,4'-bipyridin]-5-yl)-N-(5-(pyrazin-2-yl)pyridin-2-yl)acetamide, or a pharmaceutically acceptable salt thereof, is administered during the first cycle only. The present invention also provides that (i) 2-(2',3-dimethyl-[2,4'-bipyridin]-5-yl)-N-(5-(pyrazin-2-yl)pyridin-2-yl)acetamide, or a pharmaceutically acceptable salt thereof, is administered during four cycles only. The Wnt inhibitor as disclosed herein can be administered once daily or twice daily with a 12-hour gap between two consecutive doses. The combination partner (ii) an anti-PD-1 antibody molecule can continue to be administered for more cycles as long as it is clinically meaningful. In one embodiment, the (ii) anti-PD-1 antibody molecule is administered for up to 4 cycles or for 4 cycles.

The combination partners, as disclosed herein, are administered on the same day or on different days of a cycle. The term "cycle" refers to a specific period of time expressed in days or months that is repeated on a regular schedule. The cycle as disclosed herein is more preferably expressed in days. For example, the cycle can be, but is not limited to, 28 days, 30 days, 60 days, 90 days. Most preferably, the "cycle" as referred to in the present disclosure is 28 days long. Such cycle can be repeated several time (e.g. 2 times, 3 times, 4 times, 5 times, etc. . . . ), each cycle being the same length and can be repeated as long as it is clinically meaningful, i.e. the tumor growth is at least reduced, or controlled, or the tumor shrinks, and the adverse events are tolerable. While one of the combination partners, e.g. the Wnt inhibitor, is administered for up to 4 cycles, the other combination partner can continue to be administered for more cycles. The treatment by administering (i) of the present disclosure is most preferably repeated for up to 4 cycles, particularly 4 cycles. Even though the Wnt inhibitor can be administered for up to 4 cycles, it is contemplated herein that after a period of time—for example, when the compound has been completely eliminated from the body and the Wnt inhibitor that has been administered for up to 4 cycled cease to bring any positive effects, either alone or via enhancement of the effects caused by the anti-PD-1 antibody molecule, the Wnt inhibitor can again be administered for another row of up to 4 cycles. The period between the first row of up to 4 cycles (including only 1 cycle or only 4 cycles) and the second or later row of up to 4 cycles has to be long enough to prevent any accumulation of effects brought by inhibition of Wnt pathway, such as reduction of bone density.

The Wnt inhibitor (i) 2-(2',3-dimethyl-[2,4'-bipyridin]-S-yl)-N-(5-(pyrazin-2-yl)pyridin-2-yl)acetamide, or a pharmaceutically acceptable salt thereof, can be administered orally or intravenously, most preferably orally, at a daily dose of 2.5 mg/day, 5 mg/day, 7.5 mg/day, 10 mg/day, 20 mg/day, 40 mg/day, 80 mg/day, 120 mg/day, or 180 mg/day. Preferably, the daily dose is 2.5 mg/day, 5 mg/day, or 10 mg/day. Most preferably, the daily dose is 10 mg/day.

According to the present disclosure (i) 2-(2',3-dimethyl-[2,4'-bipyridin]-5-yl)-N-(5-(pyrazin-2-yl)pyridin-2-yl)acetamide, or a pharmaceutically acceptable salt thereof, can be administered orally, for example, in a pharmaceutical composition together with an inert diluent or carrier.

In accordance with the present disclosure the anti-PD-1 antibody molecule (ii), or a pharmaceutically acceptable salt thereof, selected from nivolumab (Opdivo), pembrolizumab (Keytruda), pidilizumab, PDR-001, or a pharmaceutical salt thereof, can be used in the treatment of cancer, and is administered every two weeks or every four weeks in a cycle. Most preferably the anti-PD-1 antibody molecule PDR-001 (ii), or a pharmaceutically acceptable salt thereof, as described herein, used in the treatment of cancer. Most preferably PDR-001 (ii) is administered every four weeks. PDR-001 is administered by injection (e.g. subcutaneously or intravenously) at a dose of 300-400 mg/day. Preferably, the anti-PD-1 antibody molecule PDR-001, or a pharmaceutically acceptable salt thereof, is administered intravenously in a single dose of 300 to 400 mg/day. Most preferably, the anti-PD-1 antibody molecule PDR-001 (ii), or a pharmaceutically acceptable salt thereof, is administered in a single dose of 400 mg/day. Most preferably, the anti-PD-1 antibody molecule PDR-001, or a pharmaceutically acceptable salt thereof, is administered at a dose of 400 mg/day every four weeks. The dose can be administered in a single bolus or in several divided doses.

Specifically, the dosing schedule can vary from 2.5 mg/day, 5 mg/day or 10 mg/day of Wnt inhibitor of formula (i) 2-(2',3-dimethyl-[2,4'-bipyridin]-5-yl)-N-(5-(pyrazin-2-yl)pyridin-2-yl)acetamide, or a pharmaceutically acceptable salt thereof (on days 1-15 or on days 1-8 of the first cycle only or 4 cycles only or of every cycle for up to 4 cycles) and from 300 mg/day to 400 mg/day of anti-PD-1 antibody molecule (ii), or a pharmaceutically acceptable salt thereof, every two or four weeks. For example, according to the present disclosure, 2.5 mg/day of (i) 2-(2',3-dimethyl-[2,4'-bipyridin]-5-yl)-N-(5-(pyrazin-2-yl)pyridin-2-yl)acetamide, or a pharmaceutically acceptable salt thereof, is administered on days 1-8 or on days 1-15 and anti-PD-1 antibody molecule (ii), or a pharmaceutically acceptable salt thereof, is administered once every 4 weeks for 4 cycles or up to 4 cycles at a dose of 400 mg/day. Another example, according to the present disclosure, consists of administering 5 mg/day of (i) 2-(2',3-dimethyl-[2,4'-bipyridin]-5-yl)-N-(5-(pyrazin-2-yl)pyridin-2-yl)acetamide, or a pharmaceutically acceptable salt thereof, on days 1-8 or on days 1-15 and administering anti-PD-1 antibody molecule (ii), or a pharmaceutically acceptable salt thereof, once every 4 weeks for 4 cycles or up to 4 cycles at a dose of 400 mg/day. Yet another example, according to the present disclosure, provides the administration of 10 mg/day of (i) 2-(2',3-dimethyl-[2,4'-bipyridin]-5-yl)-N-(5-(pyrazin-2-yl)pyridin-2-yl)acetamide, or a pharmaceutically acceptable salt thereof on days 1-8 or on days 1-15 and anti-PD-1 antibody molecule (ii), or a pharmaceutically acceptable salt thereof, is administered once every 4 weeks for 4 cycles or up to 4 cycles at a dose of 400 mg/day.

Another example, according to the present disclosure, provides the administration of 2.5 mg/day of (i) 2-(2',3-dimethyl-[2,4'-bipyridin]-5-yl)-N-(5-(pyrazin-2-yl)pyridin-2-yl)acetamide, or a pharmaceutically acceptable salt thereof, only during cycle 1 and the administration of anti-PD-1 antibody molecule (ii), or a pharmaceutically acceptable salt thereof, every 4 weeks, at a dose of 400 mg/day. Another example, according to the present disclosure, provides administering 5 mg/day of (i) 2-(2',3-dimethyl-[2,4'-bipyridin]-5-yl)-N-(5-(pyrazin-2-yl)pyridin-2-yl)acetamide, or a pharmaceutically acceptable salt thereof, during cycle 1 only and administering an anti-PD-1 antibody molecule (ii), or a pharmaceutically acceptable salt thereof, every 4 weeks, at a dose of 400 mg/day. Yet another example, according to the present disclosure, provides the administration of 10 mg/day of (i) 2-(2',3-dimethyl-[2,4'-bipyridin]-5-yl)-N-(5-(pyrazin-2-yl)pyridin-2-yl)acetamide, or a pharmaceutically acceptable salt thereof only during cycle 1 and the administration of anti-PD-1 antibody molecule (ii), or a pharmaceutically acceptable salt thereof, every 4 weeks, at a dose of 400 mg/day.

The antibody molecules can be administered by a variety of methods known in the art, although for many therapeutic applications, the preferred route/mode of administration is intravenous injection or infusion. For example, the antibody molecules can be administered by intravenous infusion at a rate of more than 20 mg/min, e.g., 20-40 mg/min, and typically greater than or equal to 40 mg/min to reach a dose of about 300 to 400 mg/day. For intravenous injection or infusion, therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients as required, followed by filtered sterilization. Generally, dispersions are prepared by incorporating the active compound into a sterile vehicle that contains a basic dispersion medium and the required other ingredients. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

It would be understood that the route and/or mode of administration will vary depending upon the desired results. For example, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (e.g., Sustained and Controlled Release Drug Delivery Systems, J. R. Robinson, ed., Marcel Dekker, Inc., New York, 1978).

Equally, (i) 2-(2',3-dimethyl-[2,4'-bipyridin]-5-yl)-N-(5-(pyrazin-2-yl)pyridin-2-yl)acetamide, or a pharmaceutically acceptable salt thereof, in combination with anti-PD-1 antibody molecule (ii), or a pharmaceutically acceptable salt, can be used for the manufacture of a medicament for the treatment of cancer.

By the same token, the present disclosure also provides a method for the treatment of cancer, comprising administering an effective amount of the combination partners (e.g. (i) 2-(2',3-dimethyl-[2,4'-bipyridin]-5-yl)-N-(5-(pyrazin-2-yl)pyridin-2-yl)acetamide, or a pharmaceutically acceptable salt thereof and anti-PD-1 antibody molecule (ii), or a pharmaceutically acceptable salt thereof) to a patient in need thereof.

The term "patient" or "subject" refers to a warm-blooded animal. In a most preferred embodiment, the subject or patient is human. It may be a human who has been diagnosed and is in the need of treatment for a disease or disorder, as disclosed herein.

When used for the manufacture of a medicament for the treatment of cancer or in a method of treating a cancer in a patient in need thereof, (i) and (ii) can be used in doses and dosing schedules as explained above.

Most preferably the combination comprises the Wnt inhibitor (i) 2-(2',3-dimethyl-[2,4'-bipyridin]-5-yl)-N-(5-(pyrazin-2-yl)pyridin-2-yl)acetamide, or a pharmaceutically acceptable salt thereof, and anti-PD-1 antibody molecule PDR-001 (ii), or a pharmaceutically acceptable salt thereof. Both combination partners (i) and (ii) can be administered according to the doing schedule as described herein. For example (i) 2-(2',3-dimethyl-[2,4'-bipyridin]-5-yl)-N-(5-(pyrazin-2-yl)pyridin-2-yl)acetamide, or a pharmaceutically acceptable salt thereof, can be administered daily on days 1 to 15 or on days 1 to 8 of each cycle for up to 4 cycles, for example for 4 cycles or only during the first cycle. The PDR-001 (ii), or a pharmaceutically acceptable salt thereof, is administered at least once per cycle. For example, (i) 2-(2',3-dimethyl-[2,4'-bipyridin]-5-yl)-N-(5-(pyrazin-2-yl)pyridin-2-yl)acetamide, or a pharmaceutically acceptable salt thereof is administered in this specific combination at a dose of 2.5 mg/day, 5 mg/day, 7.5 mg/day, 10 mg/day, 20 mg/day, 40 mg/day, 80 mg/day, 120 mg/day, 180 mg/day. Preferably the dose is 2.5 mg/day, 5 mg/day, or 10 mg/day. Most preferably the dose is 10 mg/day. PDR-001 inhibitor (ii), or a pharmaceutically acceptable salt thereof, is administered in a single dose of 300-400 mg/day, most preferably a dose of 400 mg/day.

By the same token, the present disclosure also provides a method for the treatment of cancer, comprising administering an effective amount of the combination partners (e.g. (i) 2-(2',3-dimethyl-[2,4'-bipyridin]-5-yl)-N-(5-(pyrazin-2-yl)pyridin-2-yl)acetamide, or a pharmaceutically acceptable salt thereof and anti-PD-1 antibody molecule (ii), or a pharmaceutically acceptable salt thereof) to a patient in need thereof.

The combination partners (i) and (ii), as described herein, can be synergistically active, while causing less side effects caused by the Wnt signaling pathway inhibition such as reduced bone density.

The term "effective amount" or "therapeutically effective amount" of the combination partners of the present disclosure, refers to an amount effective, at dosages and for periods of time necessary, to achieve the desired therapeutic result. A therapeutically effective amount of the combination partners may vary according to factors such as the disease state, age, sex, and weight of the individual. A therapeutically effective amount is also one in which any toxic or detrimental effects of the combination, as described herein, is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects.

EXAMPLES

Example 1

NanoString measures gene expression for a selected panel of up to about 1000 genes. This is executed using uniquely barcoded probes that hybridize directly to target RNAs (ribonucleic acids). The RNA-probe hybrids are then run out on a gel to linearize the barcodes. These barcodes are then counted and then normalized using an internally developed pipeline.

Tumor biopsies were performed at screening and between days 8 and 28 on treatment with the Wnt inhibitor of formula (I) 2-(2',3-dimethyl-[2,4'-bipyridin]-5-yl)-N-(5-(pyrazin-2-yl)pyridin-2-yl)acetamide. Tumors were fixed in formalin and embedded in paraffin (FFPE) or directly placed in RNA Later. These samples were transferred to Genoptix where RNA was isolated for real time qPCR analyses of the pharmacodynamics (PD) marker AXIN2. Remnant RNA was transferred to the assay research laboratory (ARL) where gene expression was profiled using (2016) NanoString pan-cancer immune profiling panel as well as a custom design panel of immune-related genes. Gene expression was normalized using methods recommended by NanoString, with the exception that samples were normalized within specific indications (e.g. melanoma or pancreatic cancer samples were normalized separately) and housekeeping genes were selected using the geNorm stability metric [PMID: 12184808]. Certain genes overlapped between both panels, which we used to assess variability and other quality control parameters. QC metrics imposed by the NanoString normalization procedure and manual review of hematoxylin and eosin (H&E) stained adjacent core biopsies narrowed down the cohort to 11 paired samples. A further two samples were removed, as they were found to be outliers in principle component analyses leaving 9 paired samples for the analysis cohort. The count data described herein was normalized according to the methods recommended by NanoString with one exception, namely that the samples were normalized within the specific indications as described herein and approximately 40 housekeeping genes (defined on the NanoString website for their commercially available cancer immune panel, 2016) were used for biological normalization across samples.

Gene signatures were used before to probe the data for phenotypic changes in the tumor-immune microenvironment. It has been previously shown that in genetically engineered mice with activated WNT signaling the dendritic cells and T-cells in the tumor microenvironment are inhibited; however, it has not been shown that this effect is reversible. Therefore, our objective was to use gene expression analyses in samples from the patients treated with the Wnt inhibitor to determine the extent to which the inhibitory effects of WNT signaling in the tumor on the proximal immune cells can be reversed by pharmacological inhibition of the WNT pathway.

To understand whether the Compound of Formula (I) has effects on the tumor immune microenvironment, we looked at the relationships between immune gene expression and the PD marker AXIN2. By using this marker, we can understand the extent to which the WNT pathway has been inhibited in a given tumor. Instead of focusing on individual genes, we used the geometric average expression of sets of genes (gene signatures) that describe a particular pathway or cellular function. One gene signature is a chemokine signature that is associated with recruitment of CD8+ T-cells [PMID: 19293190] and other signature is associated with activated CD103+ dendritic cells [PMID: 25970248]. Not every subject presented with a strong inhibition of the WNT pathway as evidenced by the fold-changes observed in AXIN2 expression. Interestingly, there appears to be fairly linear relationship between AXIN2 inhibition and increased expression of the chemokine signature as well as the dendritic cell signature (see below). We observed that pharmacological inhibition of the WNT pathway resulted in concomitant stimulation of the surrounding dendritic cell population. These dendritic cells, when stimulated, function to recruit T-cells to the tumor. Importantly, this observation was made after 15 days of exposure to the Wnt inhibitor, which supported that intermittent dosing of the Compound of Formula (I) could be combined with a checkpoint inhibitor to stimulate an anti-tumor immune response in the context of tumors that previously had lacked immune infiltrate.

Figures 2, 3:
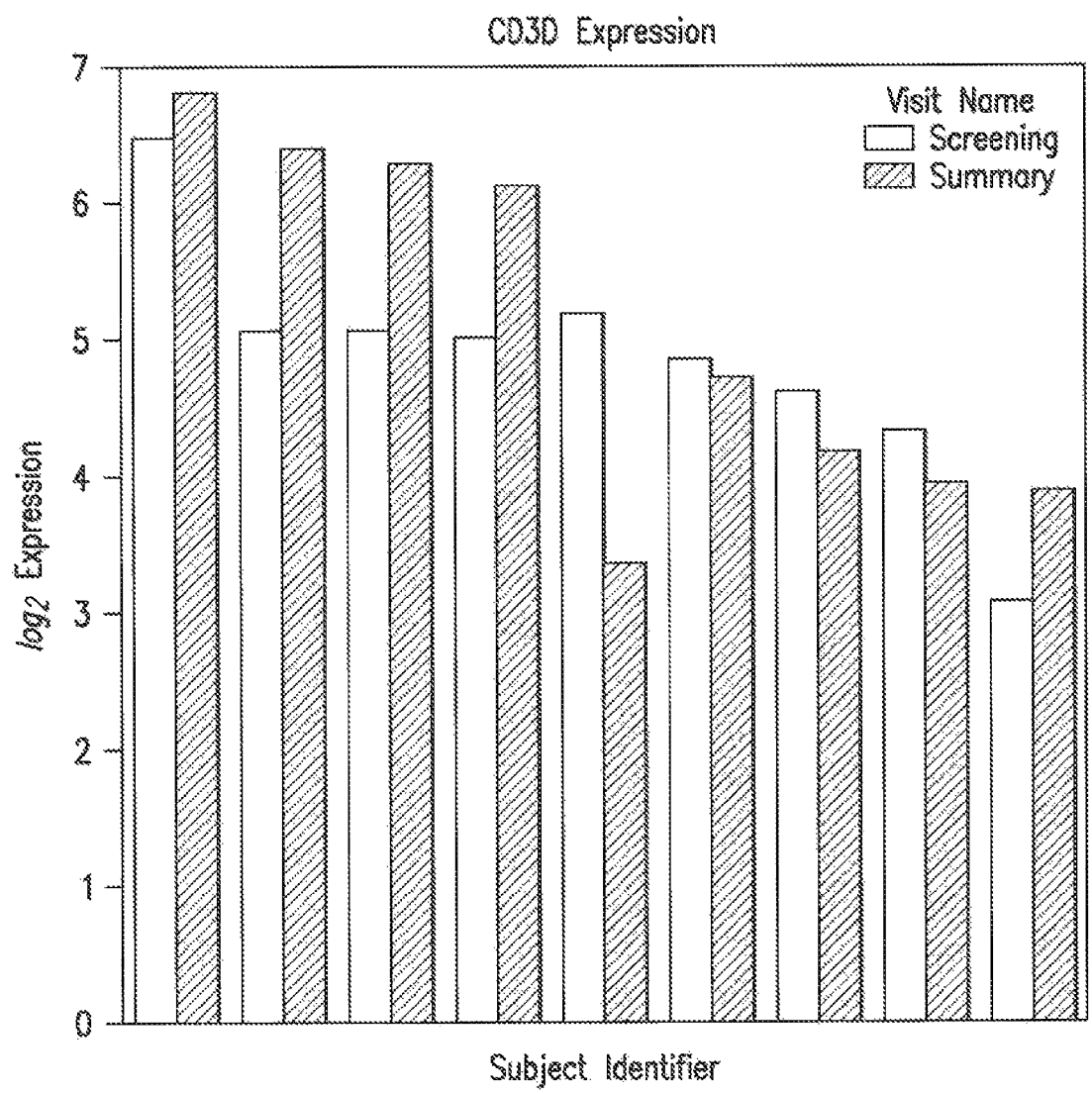
FIG. 2 shows CD3 expression at screening and summary visits for the 9 paired subjects in this analysis.
FIG. 3 shows one of the T-cell signatures selected for the study.

Gene signatures allowed us to observe a strong correlation across many samples in a given indication as well as biological relatedness even with a small sample size. The samples of the Wnt inhibitor treated patients had T-cell signatures expressed and this across patients and treatment conditions such as different dose levels (FIG. 2). FIG. 2 depicts the strong correlation between CD3 expression at screening and the T-cells levels present in summary visits for the 9 paired subjects in this analysis.

One of the gene signatures used within our study was the T-cell signature as shown in FIG. 3.

Figure 4:
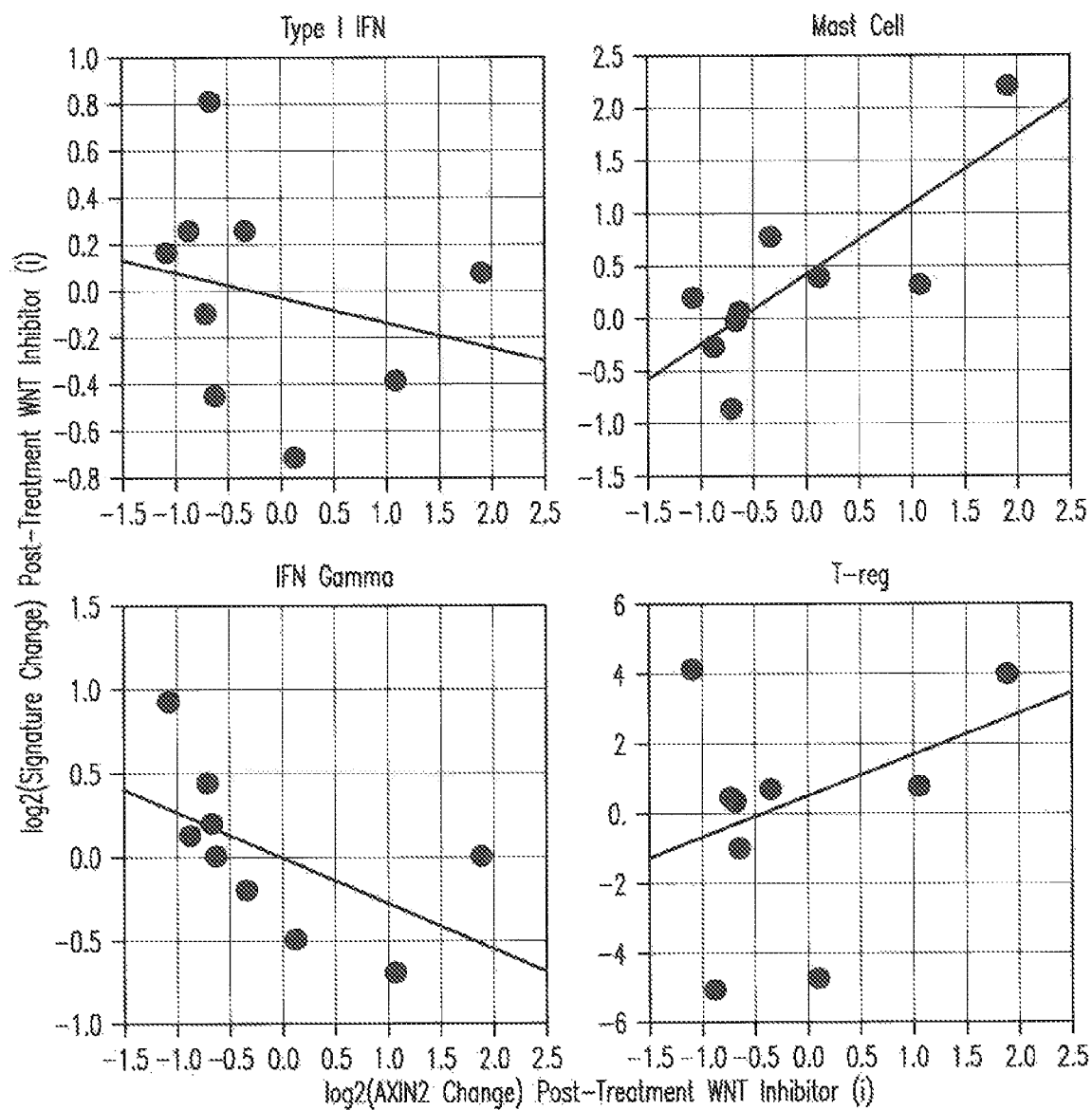
FIG. 4 shows modulation of the Wnt pathway post treatment.

Modulation on the Wnt pathway with the Wnt inhibitor of formula (i) was considered along with the way such Wnt inhibitor, namely (i) 2-(2',3-dimethyl-[2,4'-bipyridin]-5-yl)-N-(5-(pyrazin-2-yl)pyridin-2-yl)acetamide affected the tumor-immune microenvironment (FIG. 4). Changes in AXIN2 expression, which were measured by using the same exact RNA samples, were used as a measure of how Wnt inhibitor (i) 2-(2',3-dimethyl-[2,4'-bipyridin]-5-yl)-N-(5-(pyrazin-2-yl)pyridin-2-yl)acetamide affected the WNT pathway. The changes in AXIN2 expression were fitted by linear model to immune signature changes.

Figure 5:
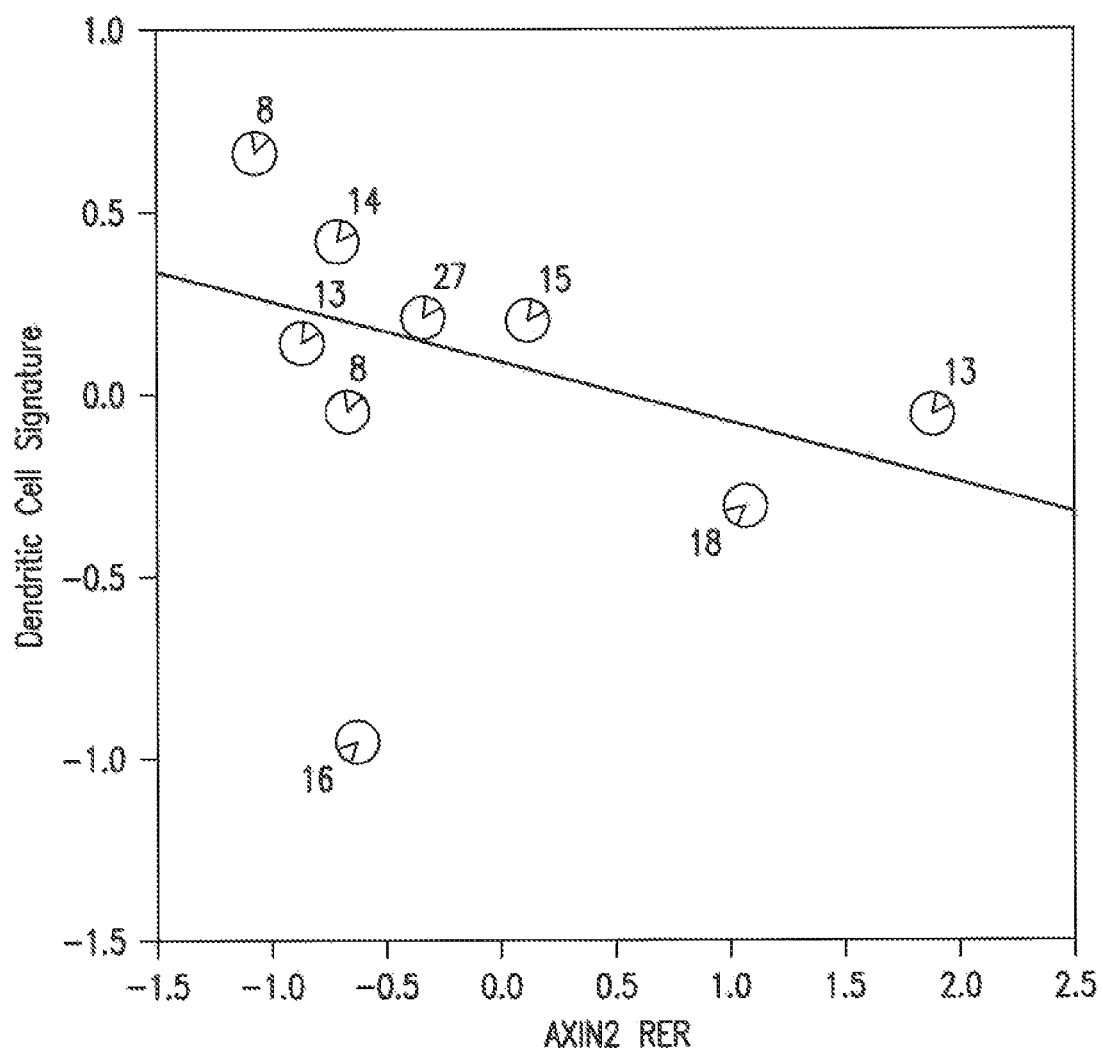
FIG. 5 shows the chemokines signature associated with the recruitment of CD103+ dentritic cells.

Each graph in FIG. 4, depicts as follows: the Y-axis depicts the change in a given immune signature after exposure to Wnt inhibitor (i) 2-(2',3-dimethyl-[2,4'-bipyridin]-5-yl)-N-(5-(pyrazin-2-yl)pyridin-2-yl)acetamide and the X-axis provides the change in AXIN2. Both are in log 2 scale. A positive value indicates an increase in the average expression of the genes in a given signature or in AXIN2. First, a weak relationship between a type I interferon signature and AXIN2 inhibition was observed. Second, a relationship between interferon gamma (or type II interferon) and AXIN2 inhibition was observed. Interferon gamma is typically expressed by CD8+ T-cells. Finally, a modest inverse relationship between AXIN2 inhibition and mast cell and T-regulation (T-reg) signatures was observed. Both of these cell types have been observed to be immunosuppressive in the tumor-immune microenvironment. Interestingly, there appears to be fairly linear relationships between AXIN2 inhibition and increased expression of the chemokine signature (FIG. 6) as well as the dendritic cell signature (FIG. 5). This is the first observation that pharmacological inhibition of the WNT pathway results in concomitant stimulation of the surrounding dendritic cell population.

Then some of the specific genes that were identified to be modulated in CD103+ dendritic cells in response to increased WNT signaling (Spranger et al., Nature 2015, 523, 231) were used to create a specific signature of sorts and model this against AXIN2 inhibition (FIG. 5). In FIG. 5, each point represents a pair of samples from one patient. Plotted on the X-axis is the log 2 fold-change in AXIN2 expression in the tumor from screening to on-treatment. Plotted on the Y-axis is the log 2 fold-change in expression of the dendritic cell signature in the tumor from screening to on-treatment. The genes included in the dendritic signature are: BATF3, ITGAE, IRF8, CCR5, CCL3, CCL4, CXCL1. The trend line is a linear estimate made by regression of the data points using a robust linear model. The numbers next to each point represent the number of days between the start of treatment and the on-treatment biopsy. According to the Spranger et al (Nature 2015, 523, 231) the genes that are Wnt-responsive are BATF3, ITGAE, IRF8, CCR5, CCL3, CCL4, CXCL1. Here, similar to some of the other signatures, a positive relationship between AXIN2 inhibition and increased expression of genes associated with activation of CD103+ dendritic cells were observed. This is relevant because this subtype of dendritic cell is important for licensing and activating T cells for an anti-tumoral response.

These data suggest that the Wnt inhibitor (i) 2-(2',3-dimethyl-[2,4'-bipyridin]-5-yl)-N-(5-(pyrazin-2-yl)pyridin-2-yl)acetamide, or a pharmaceutically acceptable salt thereof, is affecting the tumor-immune microenvironment by increasing immune cell infiltrates and alleviating the inhibition of CD103+ dendritic cells. These cells are important for activation and recruitment of cytotoxic T cells that drive the anti-tumor immune response. This supports adding an anti PD-1 antibody molecule (also referred to as PD-1 inhibitor), which alleviates the inhibition of T cells, to synergize with the effect of a Wnt inhibitor on the dendritic cells.

Figure 6:
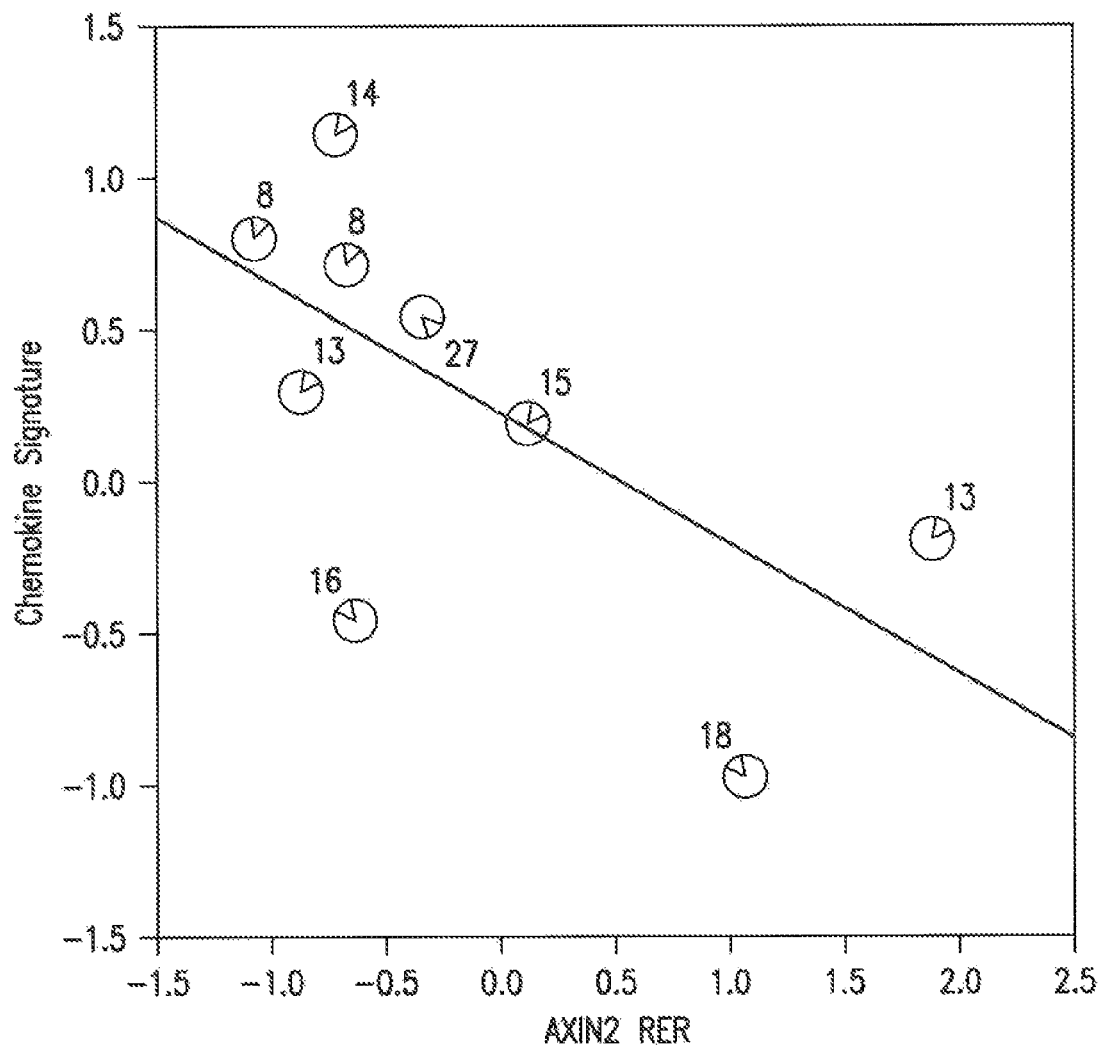
FIG. 6 shows the chemokines signature associated with the recruitment of CD8+ T-cells.

Another gene signature that was discovered to be strongly correlated with the recruitment of CD8+ T cells into the tumor was also investigated. This gene signature is made up primarily of chemokines and has some overlap with the Spranger et al (Nature 2015, 523, 231) dendritic cell signature mentioned above. These chemokines have been shown to recruit CD8+ T cells in a dose-dependent manner. The chemokines that correlate with the CD8+ T-cell recruitment are CCL2, CCL3, CCL4, CCL5, CXCL9 and CXCL10. When we measured in patient samples the average expression of the genes in this chemokine signature and compared them to AXIN2 inhibition, again we observed a linear relationship between the extent to which the WNT pathway was inhibited and the expression of this gene signature (FIG. 6). In FIG. 6, each point represents a pair of samples from one patient. Plotted on the X-axis is the log 2 fold-change in AXIN2 expression in the tumor from screening to on-treatment. Plotted on the Y-axis is the log 2 fold-change in expression of the chemokine signature in the tumor from screening to on-treatment. The genes included in the chemokine signature are: CCL2, CCL3, CCL4, CCL5, CXCL9, and CXCL10. The trend line is a linear estimate made by regression of the data points using a robust linear model. The numbers next to each point represent the number of days between the start of treatment and the on-treatment biopsy. As shown in FIG. 6, the dendritic cells, when stimulated, function to recruit T-cells to the tumor. Importantly, this observation was made after about 15 days of exposure to WNT inhibitor (i) 2-(2',3-dimethyl-[2,4'-bipyridin]-5-yl)-N-(5-(pyrazin-2-yl)pyridin-2-yl)acetamide, or a pharmaceutically acceptable salt thereof, which suggests that intermittent dosing of WNT inhibitor (i) can be combined with a checkpoint inhibitor to stimulate an anti-tumor immune response in the context of tumors that previously lacked immune infiltrate.

Figure 7A:
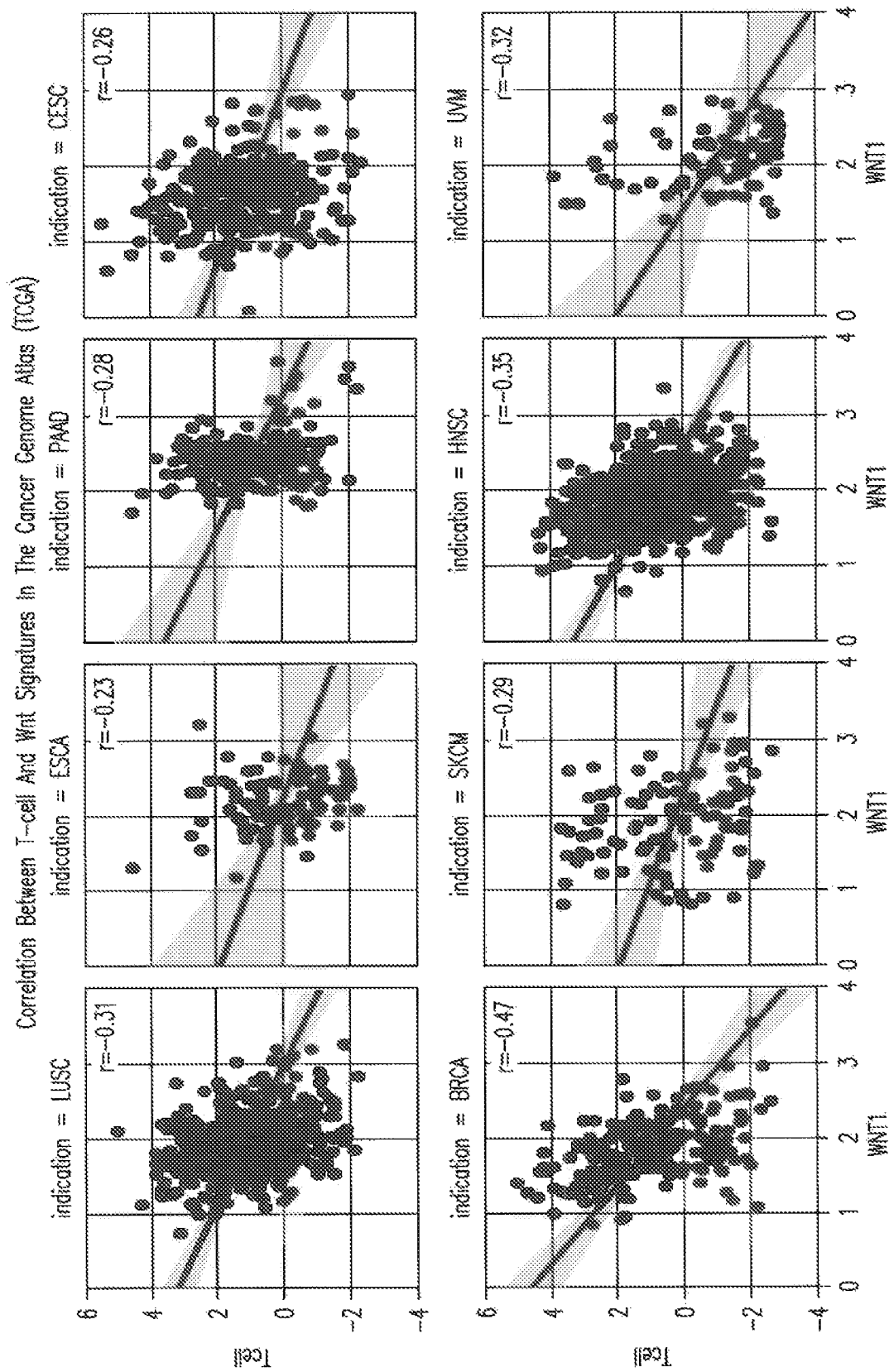
FIGS. 7A and 7B: shows the correlation between T-cell and Wnt signatures in the Cancer Genome Atlast (TCGA) for various types of cancer cells
Figure 7B:
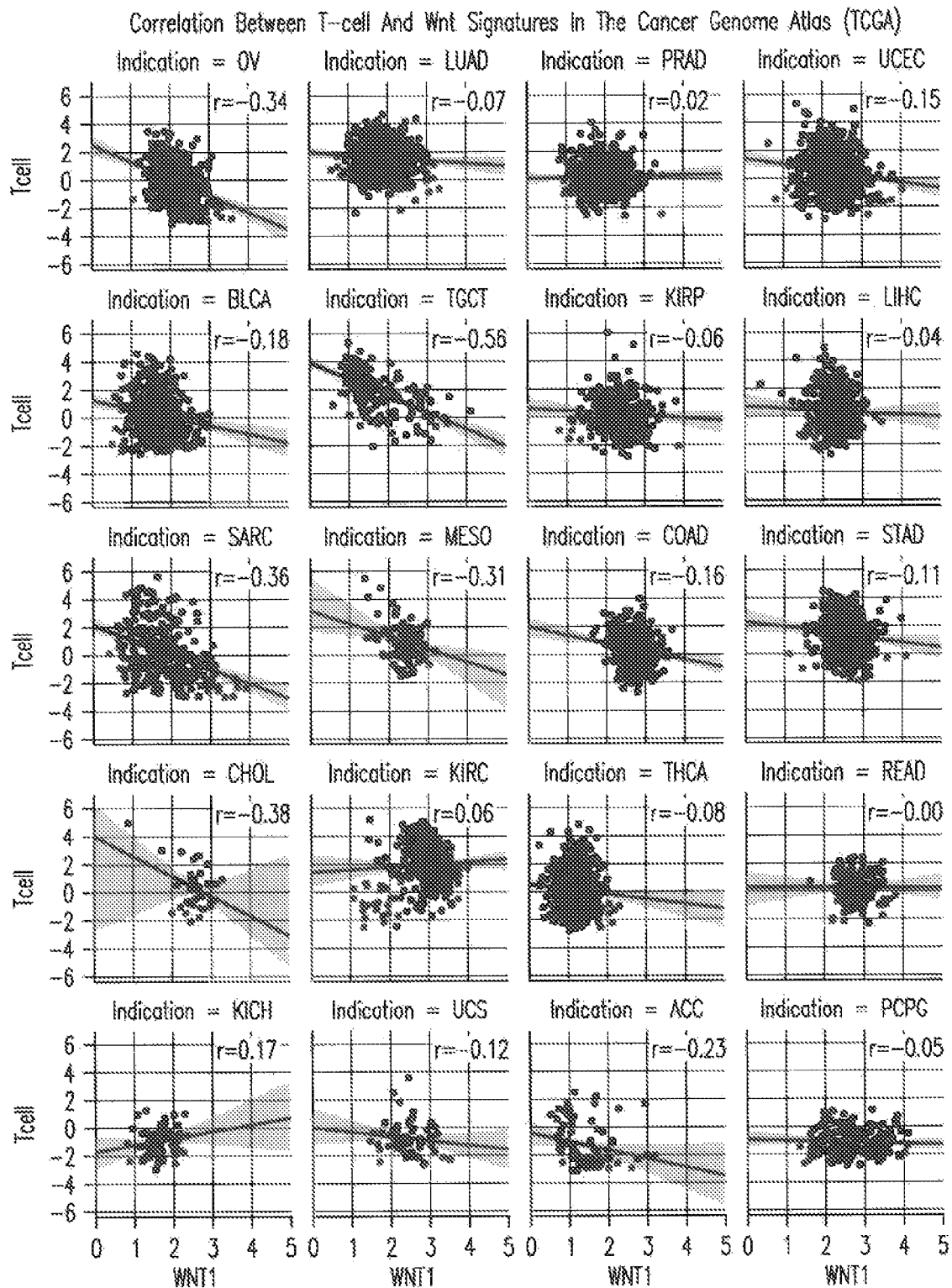

It was found that the inverse correlation between a T-cell and a Wnt/CTNNB1 signature in the Cancer Genome Atlas (TCGA) was consistent across squamous cell cancers, irrespective of the tissue of origin of the cancer cell (Sanger et al., 2015). The inverse correlation was also strong in basal-like breast cancers, which is the gene-expression based subtype most closely associated with TNBC (Bertucci et al., 2008). FIG. 7 illustrates the correlation in several different types of cancer cells. The Wnt1 signature consists of the six CTNNB1 targets: EFNB3, APC2, HNF1A, TCF12, and VEGFA.

TABLE 1

Amino acid and nucleotide sequences for humanized antibody molecules. The antibody molecules include BAP049-Clone-B and BAP049-Clone-E. The amino acid and nucleotide sequences of the heavy and light chain CDRs, the heavy and light chain variable regions, and the heavy and light chains are shown.

BAP049-Clone-B HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGS NFDEKFKNRVTITADKSTSTAYMELSSLRSE DTAVYYCTRWTTGTGAYWGQGTTVTVSS |
| SEQ ID NO: 95 | DNA VH | GAGGTGCAGCTGGTGCAGTCAGGCGCCG AAGTGAAGAAGCCCGGCGAGTCACTGAG AATTAGCTGTAAAGGTTCAGGCTACACCT TCACTACCTACTGGATGCACTGGGTCCGC CAGGCTACCGGTCAAGGCCTCGAGTGGA TGGGTAATATCTACCCCGGCACCGGCGG CTCTAACTTCGACGAGAAGTTTAAGAATA GAGTGACTATCACCGCCGATAAGTCTACT AGCACCGCCTATATGGAACTGTCTAGCCT GAGATCAGAGGACACCGCCGTCTACTACT GCACTAGGTGGACTACCGGCACAGGCGC CTACTGGGGTCAAGGCACTACCGTGACC GTGTCTAGC |
| SEQ ID NO: 91 | HC | EVQLVQSGAEVKKPGESLRISCKGSGYTFT TYWMHWVRQATGQGLEWMGNIYPGTGGS NFDEKFKNRVTITADKSTSTAYMELSSLRSE DTAVYYCTRWTTGTGAYWGQGTTVTVSSA STKGPSVFPLAPCSRSTSESTAALGCLVKD YFPEPVTVSWNSGALTSGVHTFPAVLQSSG LYSLSSVVTVPSSSLGTKTYTCNVDHKPSN TKVDKRVESKYGPPCPPCPAPEFLGGPSVF LFPPKPKDTLMISRTPEVTCVVVDVSQEDP EVQFNWYVDGVEVHNAKTKPREEQFNSTY RVVSVLTVLHQDWLNGKEYKCKVSNKGLP SSIEKTISKAKGQPREPQVYTLPPSQEEMTK NQVSLTCLVKGFYPSDIAVEWESNGQPENN YKTTPPVLDSDGSFFLYSRLTVDKSRWQEG NVFSCSVMHEALHNHYTQKSLSLSLG |
| SEQ ID NO: 96 | DNA HC | GAGGTGCAGCTGGTGCAGTCAGGCGCCG AAGTGAAGAAGCCCGGCGAGTCACTGAG AATTAGCTGTAAAGGTTCAGGCTACACCT TCACTACCTACTGGATGCACTGGGTCCGC CAGGCTACCGGTCAAGGCCTCGAGTGGA TGGGTAATATCTACCCCGGCACCGGCGG CTCTAACTTCGACGAGAAGTTTAAGAATA GAGTGACTATCACCGCCGATAAGTCTACT AGCACCGCCTATATGGAACTGTCTAGCCT GAGATCAGAGGACACCGCCGTCTACTACT GCACTAGGTGGACTACCGGCACAGGCGC CTACTGGGGTCAAGGCACTACCGTGACC |

TABLE 1-continued

Amino acid and nucleotide sequences for humanized antibody molecules. The antibody molecules include BAP049-Clone-B and BAP049-Clone-E. The amino acid and nucleotide sequences of the heavy and light chain CDRs, the heavy and light chain variable regions, and the heavy and light chains are shown.

```
GTGTCTAGCGCTAGCACTAAGGGCCCGT
CCGTGTTCCCCCTGGCACCTTGTAGCCG
GAGCACTAGCGAATCCACCGCTGCCCTC
GGCTGCCTGGTCAAGGATTACTTCCCGG
AGCCCGTGACCGTGTCCTGGAACAGCGG
AGCCCTGACCTCCGGAGTGCACACCTTC
CCCGCTGTGCTGCAGAGCTCCGGGCTGT
ACTCGCTGTCGTCGGTGGTCACGGTGCC
TTCATCTAGCCTGGGTACCAAGACCTACA
CTTGCAACGTGGACCACAAGCCTTCCAAC
ACTAAGGTGGACAAGCGCGTCGAATCGA
AGTACGGCCCACCGTGCCCGCCTTGTCC
CGCGCCGGAGTTCCTCGGCGGTCCCTCG
GTCTTTCTGTTCCCACCGAAGCCCAAGGA
CACTTTGATGATTTCCCGCACCCCTGAAG
TGACATGCGTGGTCGTGGACGTGTCACA
GGAAGATCCGGAGGTGCAGTTCAATTGG
TACGTGGATGGCGTCGAGGTGCACAACG
CCAAAACCAAGCCGAGGGAGGAGCAGTT
CAACTCCACTTACCGCGTCGTGTCCGTGC
TGACGGTGCTGCATCAGGACTGGCTGAA
CGGGAAGGAGTACAAGTGCAAAGTGTCC
AACAAGGGACTTCCTAGCTCAATCGAAAA
GACCATCTCGAAAGCCAAGGGACAGCCC
CGGGAACCCCAAGTGTATACCCTGCCAC
CGAGCCAGGAAGAAATGACTAAGAACCAA
GTCTCATTGACTTGCCTTGTGAAGGGCTT
CTACCCATCGGATATCGCCGTGGAATGG
GAGTCCAACGGCCAGCCGGAAAACAACT
ACAAGACCACCCCTCCGGTGCTGGACTC
AGACGGATCCTTCTTCCTCTACTCGCGGC
TGACCGTGGATAAGAGCAGATGGCAGGA
GGGAAATGTGTTCAGCTGTTCTGTGATGC
ATGAAGCCCTGCACAACCACTACACTCAG
AAGTCCCTGTCCCTCTCCCTGGGA
```

BAP049-Clone-B LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 54 | VL | EIVLTQSPATLSLSPGERATLSCKSSQSLLD SGNQKNFLTWYQQKPGKAPKLIIYWASTR ESGVPSRFSGSGSGTDFTFTISSLQPEDIAT YYCQNDYSYPYTFGQGTKVEIK |
| SEQ ID NO: 97 | DNA VL | GAGATCGTCCTGACTCAGTCACCCGCTAC CCTGAGCCTGAGCCCTGGCGAGCGGGCT ACACTGAGCTGTAAATCTAGTCAGTCACT GCTGGATAGCGGTAATCAGAAGAACTTCC TGACCTGGTATCAGCAGAAGCCCGGTAAA GCCCCTAAGCTGCTGATCTACTGGGCCTC TACTAGAGAATCAGGCGTGCCCTCTAGGT TTAGCGGTAGCGGTAGTGGCACCGACTT CACCTTCACTATCTCTAGCCTGCAGCCCG AGGATATCGCTACCTACTACTGTCAGAAC GACTATAGCTACCCCTACACCTTCGGTCA AGGCACTAAGGTCGAGATTAAG |
| SEQ ID NO: 56 | LC | EIVLTQSPATLSLSPGERATLSCKSSQSLLD SGNQKNFLTWYQQKPGKAPKLLIYWASTR ESGVPSRFSGSGSGTDFTFTISSLQPEDIAT YYCQNDYSYPYTFGQGTKVEIKRTVAAPSV FIFPPSDEQLKSGTASVVCLLNNFYPREAKV QWKVDNALQSGNSQESVTEQDSKDSTYSL SSTLTLSKADYEKHKVYACEVTHQGLSSPV TKSFNRGEC |
| SEQ ID NO: 98 | DNA LC | GAGATCGTCCTGACTCAGTCACCCGCTAC CCTGAGCCTGAGCCCTGGCGAGCGGGCT ACACTGAGCTGTAAATCTAGTCAGTCACT GCTGGATAGCGGTAATCAGAAGAACTTCC TGACCTGGTATCAGCAGAAGCCCGGTAAA GCCCCTAAGCTGCTGATCTACTGGGCCTC TACTAGAGAATCAGGCGTGCCCTCTAGGT |

TABLE 1-continued

Amino acid and nucleotide sequences for humanized antibody molecules. The antibody molecules include BAP049-Clone-B and BAP049-Clone-E. The amino acid and nucleotide sequences of the heavy and light chain CDRs, the heavy and light chain variable regions, and the heavy and light chains are shown.

| | | |
|---|---|---|
| | | TTAGCGGTAGCGGTAGTGGCACCGACTT<br>CACCTTCACTATCTCTAGCCTGCAGCCCG<br>AGGATATCGCTACCTACTACTGTCAGAAC<br>GACTATAGCTACCCCTACACCTTCGGTCA<br>AGGCACTAAGGTCGAGATTAAGCGTACG<br>GTGGCCGCTCCCAGCGTGTTCATCTTCCC<br>CCCCAGCGACGAGCAGCTGAAGAGCGGC<br>ACCGCCAGCGTGGTGTGCCTGCTGAACA<br>ACTTCTACCCCGGGAGGCCAAGGTGCA<br>GTGGAAGGTGGACAACGCCCTGCAGAGC<br>GGCAACAGCCAGGAGAGCGTCACCGAGC<br>AGGACAGCAAGGACTCCACCTACAGCCT<br>GAGCAGCACCCTGACCCTGAGCAAGGCC<br>GACTACGAGAAGCATAAGGTGTACGCCT<br>GCGAGGTGACCCACCAGGGCCTGTCCAG<br>CCCCGTGACCAAGAGCTTCAACAGGGGC<br>GAGTGC |
| SEQ ID NO: 92 | DNA HC | GAAGTGCAGCTGGTGCAGTCTGGCGCCG<br>AAGTGAAGAAGCCTGGCGAGTCCCTGCG<br>GATCTCCTGCAAGGGCTCTGGCTACACCT<br>TCACCACCTACTGGATGCACTGGGTGCG<br>ACAGGCTACCGGCCAGGGCCTGGAATGG<br>ATGGGCAACATCTATCCTGGCACCGGCG<br>GCTCCAACTTCGACGAGAAGTTCAAGAAC<br>AGAGTGACCATCACCGCCGACAAGTCCA<br>CCTCCACCGCCTACATGGAACTGTCCTCC<br>CTGAGATCCGAGGACACCGCCGTGTACT<br>ACTGCACCCGGTGGACAACCGGCACAGG<br>CGCTTATTGGGGCCAGGGCACCACAGTG<br>ACCGTGTCCTCTGCTTCTACCAAGGGGCC<br>CAGCGTGTTCCCCCTGGCCCCCTGCTCC<br>AGAAGCACCAGCGAGAGCACAGCCGCCC<br>TGGGCTGCCTGGTGAAGGACTACTTCCC<br>CGAGCCCGTGACCGTGTCCTGGAACAGC<br>GGAGCCCTGACCAGCGGCGTGCACACCT<br>TCCCCGCCGTGCTGCAGAGCAGCGGCCT<br>GTACAGCCTGAGCAGCGTGGTGACCGTG<br>CCCAGCAGCAGCCTGGGCACCAAGACCT<br>ACACCTGTAACGTGGACCACAAGCCCAG<br>CAACACCAAGGTGGACAAGAGGGTGGAG<br>AGCAAGTACGGCCCACCCTGCCCCCCCT<br>GCCCAGCCCCCGAGTTCCTGGGCGGACC<br>CAGCGTGTTCCTGTTCCCCCCCAAGCCCA<br>AGGACACCCTGATGATCAGCAGAACCCC<br>CGAGGTGACCTGTGTGGTGGTGGACGTG<br>TCCCAGGAGGACCCCGAGGTCCAGTTCA<br>ACTGGTACGTGGACGGCGTGGAGGTGCA<br>CAACGCCAAGACCAAGCCCAGAGAGGAG<br>CAGTTTAACAGCACCTACCGGGTGGTGTC<br>CGTGCTGACCGTGCTGCACCAGGACTGG<br>CTGAACGGCAAAGAGTACAAGTGTAAGGT<br>CTCCAACAAGGGCCTGCCAAGCAGCATC<br>GAAAAGACCATCAGCAAGGCCAAGGGCC<br>AGCCTAGAGAGCCCCAGGTCTACACCCT<br>GCCACCCAGCCAAGAGGAGATGACCAAG<br>AACCAGGTGTCCCTGACCTGTCTGGTGAA<br>GGGCTTCTACCCAAGCGACATCGCCGTG<br>GAGTGGGAGAGCAACGGCCAGCCCGAGA<br>ACAACTACAAGACCACCCCCCAGTGCTG<br>GACAGCGACGGCAGCTTCTTCCTGTACA<br>GCAGGCTGACCGTGGACAAGTCCAGATG<br>GCAGGAGGGCAACGTCTTTAGCTGCTCC<br>GTGATGCACGAGGCCCTGCACAACCACT<br>ACACCCAGAAGAGCCTGAGCCTGTCCCT<br>GGGC |

BAP049-Clone-E LC

| | | | |
|---|---|---|---|
| SEQ ID NO: 10 | (Kabat) | LCDR1 | KSSQSLLDSGNQKNFLT |
| SEQ ID NO: 11 | (Kabat) | LCDR2 | WASTRES |
| SEQ ID NO: 32 | (Kabat) | LCDR3 | QNDYSYPYT |
| SEQ ID NO: 13 | (Chothia) | LCDR1 | SQSLLDSGNQKNF |
| SEQ ID NO: 14 | (Chothia) | LCDR2 | WAS |
| SEQ ID NO: 33 | (Chothia) | LCDR3 | DYSYPY |
| SEQ ID NO: 70 | | VL | EIVLTQSPATLSLSPGERATLSCKSSQSLLD |

TABLE 1-continued

Amino acid and nucleotide sequences for humanized antibody molecules. The antibody molecules include BAP049-Clone-B and BAP049-Clone-E. The amino acid and nucleotide sequences of the heavy and light chain CDRs, the heavy and light chain variable regions, and the heavy and light chains are shown.

| | | |
|---|---|---|
| | | SGNQKNFLTWYQQKPGQAPRLLIYWASTR ESGVPSRFSGSGSGTDFTFTISSLEAEDAA TYYCQNDYSYPYTFGQGTKVEIK |
| SEQ ID NO: 106 | DNA VL | GAGATCGTCCTGACTCAGTCACCCGCTAC CCTGAGCCTGAGCCCTGGCGAGCGGGCT ACACTGAGCTGTAAATCTAGTCAGTCACT GCTGGATAGCGGTAATCAGAAGAACTTCC TGACCTGGTATCAGCAGAAGCCCGGTCA AGCCCCTAGACTGCTGATCTACTGGGCCT CTACTAGAGAATCAGGCGTGCCCTCTAGG TTTAGCGGTAGCGGTAGTGGCACCGACTT CACCTTCACTATCTCTAGCCTGGAAGCCG AGGACGCCGCTACCTACTACTGTCAGAAC GACTATAGCTACCCCTACACCTTCGGTCA AGGCACTAAGGTCGAGATTAAG |
| SEQ ID NO: 72 | LC | EIVLTQSPATLSLSPGERATLSCKSSQSLLD SGNQKNFLTWYQQKPGQAPRLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREAK VQWKVDNALQSGNSQESVTEQDSKDSTYS LSSTLTLSKADYEKHKVYACEVTHQGLSSP VTKSFNRGEC |
| SEQ ID NO: 107 | DNA LC | GAGATCGTCCTGACTCAGTCACCCGCTAC CCTGAGCCTGAGCCCTGGCGAGCGGGCT ACACTGAGCTGTAAATCTAGTCAGTCACT GCTGGATAGCGGTAATCAGAAGAACTTCC TGACCTGGTATCAGCAGAAGCCCGGTCA AGCCCCTAGACTGCTGATCTACTGGGCCT CTACTAGAGAATCAGGCGTGCCCTCTAGG TTTAGCGGTAGCGGTAGTGGCACCGACTT CACCTTCACTATCTCTAGCCTGGAAGCCG AGGACGCCGCTACCTACTACTGTCAGAAC GACTATAGCTACCCCTACACCTTCGGTCA AGGCACTAAGGTCGAGATTAAGCGTACG GTGGCCGCTCCCAGCGTGTTCATCTTCCC CCCCAGCGACGAGCAGCTGAAGAGCGGC ACCGCCAGCGTGGTGTGCCTGCTGAACA ACTTCTACCCCGGGAGGCCAAGGTGCA GTGGAAGGTGGACAACGCCCTGCAGAGC GGCAACAGCCAGGAGAGCGTCACCGAGC AGGACAGCAAGGACTCCACCTACAGCCT GAGCAGCACCCTGACCCTGAGCAAGGCC GACTACGAGAAGCATAAGGTGTACGCCT GCGAGGTGACCCACCAGGGCCTGTCCAG CCCCGTGACCAAGAGCTTCAACAGGGGC GAGTGC |

BAP049-Clone-B HC

| | | |
|---|---|---|
| SEQ ID NO: 133 (Kabat) | HCDR1 | ACCTACTGGATGCAC |
| SEQ ID NO: 134 (Kabat) | HCDR2 | AATATCTACCCCGGCACCGGCGGCTCTAA CTTCGACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |

BAP049-Clone-B LC

| | | |
|---|---|---|
| SEQ ID NO: 138 (Kabat) | LCDR1 | AAATCTAGTCAGTCACTGCTGGATAGCGG TAATCAGAAGAACTTCCTGACC |
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCA GAAGAACTTC |
| SEQ ID NO: 142 (Chothia) | LCDR2 | TGGGCCTCT |
| SEQ ID NO: 143 (Chothia) | LCDR3 | GACTATAGCTACCCCTAC |

BAP049-Clone-E HC

| | | |
|---|---|---|
| SEQ ID NO: 133 (Kabat) | HCDR1 | ACCTACTGGATGCAC |
| SEQ ID NO: 134 (Kabat) | HCDR2 | AATATCTACCCCGGCACCGGCGGCTCTAA CTTCGACGAGAAGTTTAAGAAT |
| SEQ ID NO: 135 (Kabat) | HCDR3 | TGGACTACCGGCACAGGCGCCTAC |

TABLE 1-continued

Amino acid and nucleotide sequences for humanized antibody molecules. The antibody molecules include BAP049-Clone-B and BAP049-Clone-E. The amino acid and nucleotide sequences of the heavy and light chain CDRs, the heavy and light chain variable regions, and the heavy and light chains are shown.

| SEQ ID NO: 136 (Chothia) | FiCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |

BAP049-Clone-E LC

| SEQ ID NO: 138 (Kabat) | LCDR1 | AAATCTAGTCAGTCACTGCTGGATAGCGG TAATCAGAAGAACTTCCTGACC |
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCA GAAGAACTTC |
| SEQ ID NO: 142 (Chothia) | LCDR2 | TGGGCCTCT |
| SEQ ID NO: 143 (Chothia) | LCDR3 | GACTATAGCTACCCCTAC |

TABLE 2

Amino acid and nucleotide sequences of the heavy and light chain framework regions for humanized mAbs BAP049-Clone-B and BAP049-Clone-E

| | Amino Acid Sequence | Nucleotide Sequence |
| --- | --- | --- |
| VHFW1 (type a) | EVQLVQSGAEVKKPGESLRISCKGS (SEQ ID NO: 147) | GAAGTGCAGCTGGTGCAGTCTGGAGCAGA GGTGAAAAAGCCCGGGGAGTCTCTGAGGAT CTCCTGTAAGGGTTCT (SEQ ID NO: 148) GAAGTGCAGCTGGTGCAGTCTGGCGCCGA AGTGAAGAAGCCTGGCGAGTCCCTGCGGAT CTCCTGCAAGGGCTCT (SEQ ID NO: 149) GAGGTGCAGCTGGTGCAGTCAGGCGCCGA AGTGAAGAAGCCCGGCGAGTCACTGAGAAT TAGCTGTAAAGGTTCA (SEQ ID NO: 150) |
| VHFW1 (type b) | QVQLVQSGAEVKKPGASVKVSCKA S (SEQ ID NO: 151) | CAGGTTCAGCTGGTGCAGTCTGGAGCTGAG GTGAAGAAGCCTGGGGCCTCAGTGAAGGTC TCCTGCAAGGCTTCT (SEQ ID NO: 152) |
| VHFW2 (type a) | WVRQATGQGLEWMG (SEQ ID NO: 153) | TGGGTGCGACAGGCCACTGGACAAGGGCT TGAGTGGATGGGT (SEQ ID NO: 154) TGGGTGCGACAGGCTACCGGCCAGGGCCT GGAATGGATGGGC (SEQ ID NO: 155) TGGGTCCGCCAGGCTACCGGTCAAGGCCT CGAGTGGATGGGT (SEQ ID NO: 156) |
| VHFW2 (type b) | WIRQSPSRGLEWLG (SEQ ID NO: 157) | TGGATCAGGCAGTCCCCATCGAGAGGCCTT GAGTGGCTGGGT (SEQ ID NO: 158) TGGATCCGGCAGTCCCCCTCTAGGGGCCTG GAATGGCTGGGC (SEQ ID NO: 159) |
| VHFW2 (type c) | WVRQAPGQGLEWMG (SEQ ID NO: 160) | TGGGTGCGACAGGCCCCTGGACAAGGGCT TGAGTGGATGGGT (SEQ ID NO: 161) |
| VHFW3 (type a) | RVTITADKSTSTAYMELSSLRSEDTA VYYCTR (SEQ ID NO: 162) | AGAGTCACGATTACCGCGGACAAATCCACG AGCACAGCCTACATGGAGCTGAGCAGCCTG AGATCTGAGGACACGGCCGTGTATTACTGT ACAAGA (SEQ ID NO: 163) AGAGTGACCATCACCGCCGACAAGTCCACC TCCACCGCCTACATGGAACTGTCCTCCCTG AGATCCGAGGACACCGCCGTGTACTACTGC ACCCGG (SEQ ID NO: 164) AGAGTGACTATCACCGCCGATAAGTCTACTA GCACCGCCTATATGGAACTGTCTAGCCTGA GATCAGAGGACACCGCCGTCTACTACTGCA CTAGG (SEQ ID NO: 165) |
| VHFW3 (type b) | RFTISRDNSKNTLYLQMNSLRAEDT AVYYCTR (SEQ ID NO: 166) | AGATTCACCATCTCCAGAGACAATTCCAAGA ACACGCTGTATCTTCAAATGAACAGCCTGAG AGCCGAGGACACCGGCCGTGTATTACTGTAC AAGA (SEQ ID NO: 167) AGGTTCACCATCTCCCGGGACAACTCCAAG AACACCCTGTACCTGCAGATGAACTCCCTG CGGGCCGAGGACACCGCCGTGTACTACTGT ACCAGA (SEQ ID NO: 168) |

TABLE 2-continued

Amino acid and nucleotide sequences of the heavy and light chain framework regions for humanized mAbs BAP049-Clone-B and BAP049-Clone-E

| | Amino Acid Sequence | Nucleotide Sequence |
|---|---|---|
| VHFW4 | WGQGTTVTVSS (SEQ ID NO: 169) | TGGGGCCAGGGCACCACCGTGACCGTGTCCTCC (SEQ ID NO: 170)<br>TGGGGCCAGGGCACCACAGTGACCGTGTCCTCT (SEQ ID NO: 171)<br>TGGGGTCAAGGCACTACCGTGACCGTGTCTAGC (SEQ ID NO: 172)<br>TGGGGCCAGGGCACAACAGTGACCGTGTCCTCC (SEQ ID NO: 173) |
| VLFW1 (type a) | EIVLTQSPDFQSVTPKEKVTITC (SEQ ID NO: 174) | GAAATTGTGCTGACTCAGTCTCCAGACTTTCAGTCTGTGACTCCAAAGGAGAAAGTCACCATCACCTGC (SEQ ID NO: 175)<br>GAGATCGTGCTGACCCAGTCCCCCGACTTCCAGTCCGTGACCCCCAAAGAAAAAGTGACCATCACATGC (SEQ ID NO: 176) |
| VLFW1 (type b) | EIVLTQSPATLSLSPGERATLSC (SEQ ID NO: 177) | GAAATTGTGTTGACACAGTCTCCAGCCACCCTGTCTTTGTCTCCAGGGGAAAGAGCCACCCTCTCCTGC (SEQ ID NO: 178)<br>GAGATCGTGCTGACCCAGTCCCCTGCCACCCTGTCACTGTCTCCAGGCGAGAGAGCTACCCTGTCCTGC (SEQ ID NO: 179)<br>GAGATCGTCCTGACTCAGTCACCCGCTACCCTGAGCCTGAGCCCTGGCGAGCGGGCTACACTGAGCTGT (SEQ ID NO: 180) |
| VLFW1 (type c) | DIVMTQTPLSLPVTPGEPASISC (SEQ ID NO: 181) | GATATTGTGATGACCCAGACTCCACTCTCCCTGCCCGTCACCCCTGGAGAGCCGGCCTCCATCTCCTGC (SEQ ID NO: 182) |
| VLFW1 (type d) | DVVMTQSPLSLPVTLGQPASISC (SEQ ID NO: 183) | GATGTTGTGATGACTCAGTCTCCACTCTCCCTGCCCGTCACCCTTGGACAGCCGGCCTCCATCTCCTGC (SEQ ID NO: 184) |
| VLFW1 (type e) | DIQMTQSPSSLSASVGDRVTITC (SEQ ID NO: 185) | GACATCCAGATGACCCAGTCTCCATCCTCCCTGTCTGCATCTGTAGGAGACAGAGTCACCATCACTTGC (SEQ ID NO: 186) |
| VLFW2 (type a) | WYQQKPGQAPRLLIY (SEQ ID NO: 187) | TGGTACCAGCAGAAACCTGGCCAGGCTCCCAGGCTCCTCATCTAT (SEQ ID NO: 188)<br>TGGTATCAGCAGAAGCCCGGCCAGGCCCCCAGACTGCTGATCTAC (SEQ ID NO: 189)<br>TGGTATCAGCAGAAGCCCGGTCAAGCCCCTAGACTGCTGATCTAC (SEQ ID NO: 190) |
| VLFW2 (type b) | WYQQKPGKAPKLLIY (SEQ ID NO: 191) | TGGTATCAGCAGAAACCAGGGAAAGCTCCTAAGCTCCTGATCTAT (SEQ ID NO: 192)<br>TGGTATCAGCAGAAGCCCGGTAAAGCCCCTAAGCTGCTGATCTAC (SEQ ID NO: 193) |
| VLFW2 (type c) | WYLQKPGQSPQLLIY (SEQ ID NO: 194) | TGGTACCTGCAGAAGCCAGGGCAGTCTCCACAGCTCCTGATCTAT (SEQ ID NO: 195) |
| VLFW3 (type a) | GVPSRFSGSGSGTDFTFTISSLEAEDAATYYC (SEQ ID NO: 196) | GGGGTCCCCTCGAGGTTCAGTGGCAGTGGATCTGGGACAGATTTCACCTTTACCATCAGTAGCCTGGAAGCTGAAGATGCTGCAACATATTACTGT (SEQ ID NO: 197)<br>GGCGTGCCCTCTAGATTCTCCGGCTCCGGCTCTGGCACCGACTTTACCTTCACCATCTCCAGCCTGGAAGCCGAGGACGCCGCCACCTACTACTGC (SEQ ID NO: 198)<br>GGCGTGCCCTCTAGGTTTAGCGGTAGCGGTAGTGGCACCGACTTCACCTTCACTATCTCTAGCCTGGAAGCCGAGGACGCCGCTACCTACTACTGT (SEQ ID NO: 199) |
| VLFW3 (type b) | GIPPRFSGSGYGTDFTLTINNIESEDAAYYFC (SEQ ID NO: 200) | GGGATCCCACCTCGATTCAGTGGCAGCGGGTATGGAACAGATTTACCCTCACAATTAATAACATAGAATCTGAGGATGCTGCATATTACTTCTGT (SEQ ID NO: 201) |

TABLE 2-continued

Amino acid and nucleotide sequences of the heavy and light chain framework regions for humanized mAbs BAP049-Clone-B and BAP049-Clone-E

|  | Amino Acid Sequence | Nucleotide Sequence |
|---|---|---|
| VLFW3 (type c) | GVPSRFSGSGSGTEFTLTISSLQPD DFATYYC (SEQ ID NO: 202) | GGGGTCCCATCAAGGTTCAGCGGCAGTGG ATCTGGGACAGAATTCACTCTCACCATCAGC AGCCTGCAGCCTGATGATTTTGCAACTTATT ACTGT (SEQ ID NO: 203) GGCGTGCCCTCTAGATTCTCCGGCTCCGGC TCTGGCACCGAGTTTACCCTGACCATCTCC AGCCTGCAGCCCGACGACTTCGCCACCTAC TACTGC (SEQ ID NO: 204) |
| VLFW3 (type d) | GVPSRFSGSGSGTDFTFTISSLQPE DIATYYC (SEQ ID NO: 205) | GGGGTCCCATCAAGGTTCAGTGGAAGTGGA TCTGGGACAGATTTTACTTTCACCATCAGCA GCCTGCAGCCTGAAGATATTGCAACATATTA CTGT (SEQ ID NO: 206) GGCGTGCCCTCTAGGTTTAGCGGTAGCGGT AGTGGCACCGACTTCACCTTCACTATCTCTA GCCTGCAGCCCGAGGATATCGCTACCTACT ACTGT (SEQ ID NO: 207) |
| VLFW4 | FGQGTKVEIK (SEQ ID NO: 208) | TTCGGCCAAGGGACCAAGGTGGAAATCAAA (SEQ ID NO: 209) TTCGGCCAGGGCACCAAGGTGGAAATCAAG (SEQ ID NO: 210) TTCGGTCAAGGCACTAAGGTCGAGATTAAG (SEQ ID NO: 211) |

TABLE 3

Constant region amino acid sequences of human IgG heavy chains and human kappa light chain HC IgG4 (S228P) mutant constant region amino acid sequence (EU Numbering)
    ASTKGPSVFP LAPCSRSTSE STAALGCLVK DYFPEPVTVS WNSGALTSGV HTFPAVLQSS
    GLYSLSSVVT VPSSSLGTKT YTCNVDHKPS NTKVDKRVES KYGPPCPPCP APEFLGGPSV
    FLFPPKPKDT LMISRTPEVT CVVVDVSQED PEVQFNWYVD GVEVHNAKTK PREEQFNSTY
    RVVSVLTVLH QDWLNGKEYK CKVSNKGLPS SIEKTISKAK GQPREPQVYT LPPSQEEMTK
    NQVSLTCLVK GFYPSDIAVE WESNGQPENN YKTTPPVLDS DGSFFLYSRL
    TVDKSRWQEG NVFSCSVMHE ALHNHYTQKS LSLSLGK (SEQ ID NO: 212)

LC Human kappa constant region amino acid sequence
    RTVAAPSVFI FPPSDEQLKS GTASVVCLLN NFYPREAKVQ WKVDNALQSG NSQESVTEQD
    SKDSTYSLSS TLTLSKADYE KHKVYACEVT HQGLSSPVTK
    SFNRGEC (SEQ ID NO: 213)

HC IgG4 (S228P) mutant constant region amino acid sequence lacing C-terminal lysine (K)
    (EU Numbering)
    ASTKGPSVFP LAPCSRSTSE STAALGCLVK DYFPEPVTVS WNSGALTSGV HTFPAVLQSS
    GLYSLSSVVT VPSSSLGTKT YTCNVDHKPS NTKVDKRVES KYGPPCPPCP APEFLGGPSV
    FLFPPKPKDT LMISRTPEVT CVVVDVSQED PEVQFNWYVD GVEVHNAKTK PREEQFNSTY
    RVVSVLTVLH QDWLNGKEYK CKVSNKGLPS SIEKTISKAK GQPREPQVYT LPPSQEEMTK
    NQVSLTCLVK GFYPSDIAVE WESNGQPENN YKTTPPVLDS DGSFFLYSRL
    TVDKSRWQEG NVFSCSVMHE ALHNHYTQKS LSLSLG (SEQ ID NO: 214)

HC IgG1 wild type
    ASTKGPSVFP LAPSSKSTSG GTAALGCLVK DYFPEPVTVS WNSGALTSGV HTFPAVLQSS
    GLYSLSSVVT VPSSSLGTQT YICNVNHKPS NTKVDKRVEP KSCDKTHTCP PCPAPELLGG
    PSVFLFPPKP KDTLMISRTP EVTCVVVDVS HEDPEVKFNW YVDGVEVHNA KTKPREEQYN
    STYRVVSVLT VLHQDWLNGK EYKCKVSNKA LPAPIEKTIS KAKGQPREPQ VYTLPPSREE
    MTKNQVSLTC LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 215)

HC IgG1 (N297A) mutant constant region amino acid sequence (EU Numbering)
    ASTKGPSVFP LAPSSKSTSG GTAALGCLVK DYFPEPVTVS WNSGALTSGV HTFPAVLQSS
    GLYSLSSVVT VPSSSLGTQT YICNVNHKPS NTKVDKRVEP KSCDKTHTCP PCPAPELLGG
    PSVFLFPPKP KDTLMISRTP EVTCVVVDVS HEDPEVKFNW YVDGVEVHNA KTKPREEQYA
    STYRVVSVLT VLHQDWLNGK EYKCKVSNKA LPAPIEKTIS KAKGQPREPQ VYTLPPSREE
    MTKNQVSLTC LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 216)

HC IgG1 (D265A, P329A) mutant constant region amino acid sequence (EU Numbering)
    ASTKGPSVFP LAPSSKSTSG GTAALGCLVK DYFPEPVTVS WNSGALTSGV HTFPAVLQSS
    GLYSLSSVVT VPSSSLGTQT YICNVNHKPS NTKVDKRVEP KSCDKTHTCP PCPAPELLGG
    PSVFLFPPKP KDTLMISRTP EVTCVVVAVS HEDPEVKFNW YVDGVEVHNA KTKPREEQYN

TABLE 3-continued

Constant region amino acid sequences of human IgG heavy chains and human kappa light chain

```
    STYRVVSVLT VLHQDWLNGK EYKCKVSNKA LAAPIEKTIS KAKGQPREPQ VYTLPPSREE
    MTKNQVSLTC LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 217)

HC IgG1 (L234A, L235A) mutant constant region amino acid sequence (EU Numbering)
    ASTKGPSVFP LAPSSKSTSG GTAALGCLVK DYFPEPVTVS WNSGALTSGV HTFPAVLQSS
    GLYSLSSVVT VPSSSLGTQT YICNVNHKPS NTKVDKRVEP KSCDKTHTCP PCPAPEAAGG
    PSVFLFPPKP KDTLMISRTP EVTCVVVDVS HEDPEVKFNW YVDGVEVHNA KTKPREEQYN
    STYRVVSVLT VLHQDWLNGK EYKCKVSNKA LPAPIEKTIS KAKGQPREPQ VYTLPPSREE
    MTKNQVSLTC LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 218)
```

TABLE 4

Amino acid sequences of the heavy and light chain leader sequences for humanized mAbs BAP049-Clone-B and BAP049-Clone-E

| | | |
|---|---|---|
| BA1049-Clone-B | HC | MAWVWTLPFLMAAAQSVQA (SEQ ID NO: 221) |
| | LC | MSVLTQVLALLLLWLTGTRC (SEQ ID NO: 222) |
| BAP049-Clone-E | HC | MAWVWTLPFLMAAAQSVQA (SEQ ID NO: 221) |
| | LC | MSVLTQVLALLLLWLTGTRC (SEQ ID NO: 222) |

Example 2: Clinical Study Summary

The following clinical study will be used to confirm the rationale, findings, and conclusions of Example 1. The safety and efficacy expected from Example 1 will also be further evaluated.

A Phase I, open-label, dose escalation study of oral LGK974 and PDR001 in patients with malignancies dependent on Wnt Ligands

| | |
|---|---|
| Purpose and rationale | The purpose of this study is to assess the recommended dose of the Compound of Formula (I) in combination with PDR001 that can be safely administered to patients with selected solid malignancies for whom no effective standard treatment is available. |
| Primary Objective | To determine the MTD and/or recommended dose for the Compound of Formula (I) in combination with PDR001 when administered to patients with malignancies dependent on Wnt ligands as specified in the inclusion criteria. |
| Secondary Objectives | To characterize the safety and tolerability of the Compound of Formula (I) in combination with PDR001.<br>To evaluate the PK of the Compound of Formula (I) in combination with PDR001<br>To assess the anti-tumor activity of the Compound of Formula (I) in combination with PDR001. |
| Study design | This is a multi-center, open-label phase 1 study. The initial dose of the Compound of Formula (I) and PDR001 in combination will be 2.5 mg QD days 1-8 day in cycle 1 only and 400 mg Q4W, respectively. The PDR001 dose of 400 mg Q4W is the RP2D determined within the CPDR001X2101 clinical study. The Compound of Formula (I) will be started at 2.5 mg QD, the −1 dose from which target inhibition is observed in the single agent portion of the study. Other schedules of the Compound of Formula (I) dosing may be explored (i.e. Cycle 1-4 LGK974 QD dosing on day 1 through day 8 each cycle; Compound of Formula (I) QD dosing on day 1-15 Cycle 1 only; or Cycle 1-4 LGK974 QD dosing on day 1 through 15 each cycle), depending on safety, PK, PD, and efficacy data. Dose escalation will continue until the MTD and/or RDE is reached. For the dose escalation part, a Bayesian logistic regression model (BLRM) with overdose control (EWOC) principle will be employed for dose level selection and determination of the MTD and/or RDE. The expansion part of the study will be initiated at the determination of the RDE and will be carried out with one regimen. The goal of the expansion part is to better characterize the safety and tolerability, PK/PD relationship as well as to explore the anti-tumor activity of the combination. Approximately 40 patients across the 4 disease areas will be treated in the dose expansion part of the study.<br>Toxicity will be evaluated according to CTCAE version 4.03 to evaluate the safety and tolerability of the Compound of Formula (I) as a single agent and in combination with PDR001. Disease response will be assessed using RECIST v1.1 within the single agent portion and RECIST v1.1 and irRC in the combination portion. |

| | A Phase I, open-label, dose escalation study of oral LGK974 and PDR001 in patients with malignancies dependent on Wnt Ligands |
|---|---|
| | Patients will be treated until disease progression or unacceptable toxicity occurs, or withdrawal of consent after which all patients will have a study evaluation completion (SEC) safety follow-up for adverse events (AEs) and serious adverse events (SAEs) for 30 days after the last dose of the Compound of Formula (I) within the single agent portion, and 150 days after last dose of PDR001 or 30 days after last dose of the Compound of Formula (I), whichever is latest within the combination portion. |
| Population | Adult and adolescent patients with advanced cancer and who have progressed despite standard therapy or for whom no effective standard therapy exists with a histologically confirmed diagnosis of:<br>the Compound of Formula (I)in combination with PDR001:<br>pancreatic adenocarcinoma<br>triple negative breast cancer (TNBC),<br>melanoma<br>head and neck squamous cell cancer<br>squamous cell cancer of the lung<br>squamous cell cancer of the esophagus<br>squamous cell cancer of the cervix |
| Inclusion criteria | Patients eligible for inclusion in this study have to meet all of the following criteria:<br>1. Diagnosis of locally advanced or metastatic cancer that has progressed despite standard therapy or for which no effective standard therapy exists and histological confirmation of one of the following diseases indicated below:<br>the Compound of Formula (I) with PDR001: Dose escalation: patients with the following cancers that were previously treated with anti-PD-1 therapy and whose best response on that therapy was progressive disease (i.e., primary refractory): melanoma, lung SCC, HNSCC. Patients with esophageal SCC, cervical SCC or TNBC regardless of prior anti-PD-1 therapy are also eligible. However, patients with esophageal SCC, cervical SCC, or TNBC who had received prior anti-PD-1 therapy must have had a best response of progressive disease to that therapy.<br>the Compound of Formula (I) with PDR001: Dose expansion: patients with pancreatic cancer, or TNBC, or melanoma or head and neck squamous cell cancer.<br>2. Age 18 years or older<br>3. WHO Performance Status of 0-2<br>4. During the dose escalation part of the study patients must have evaluable disease. During the expansion part of the study patients must have measurable disease as defined by RECIST v1.1 (at least one lesion ≥10 mm in at least one dimension when assessed by CT or MRI, or a cutaneous lesion with clearly defined margins that measures ≥10 mm in at least one dimension)<br>6. Willingness and ability to comply with all study procedures<br>7. Written informed consent obtained prior to any screening procedures<br>8. Patient must be willing to undergo a new tumor biopsy at screening. |
| Investigational and reference therapy | Investigational Drug:<br>LGK974 [2-(2',3-dimethyl-2,4'-bipyridin-5-yl)-N-(5-(pyrazin-2-yl)pyridin-2-yl) acetamide] 2.5-mg, 10-mg, and 50-mg capsule<br>PDR001: 100-mg powder for infusion |
| Efficacy assessments | Compound of Formula (I) in combination with PDR001: Tumor response will be determined by local investigator interpretation according to two sets of criteria:<br>1. RECIST v1.1<br>2. irRC<br>At baseline all patients will undergo CT with i.v. contrast of the chest, abdomen and pelvis. If there is clinical evidence of disease in the head or neck, a CT of the head and/or neck will also be performed. MRI should only be used to evaluate sites of disease that are not adequately imaged by CT. If a patient is intolerant of iodine-based contrast agents, CTs may be performed without contrast; however, MRI may be used to evaluate sites of disease where a CT without i.v. contrast is not adequate. Visible skin lesions and easily palpable subcutaneous tumors may be measured by physical examination using a ruler or calipers. Ultrasound should not be used to measure sites of disease.<br>Subsequent tumor evaluations for patients treated with the Compound of Formula (I) in combination with PDR001 will be obtained during treatment starting on Cycle 3 Day 1, every 2 cycles until Cycle 11 Day 1, and then every 3 cycles until progression of disease as per irRC or patient withdrawal and during follow-up for progession every 8 weeks for 40 week, then every 12 weeks until progression of disease per irRC or lost to follow-up. |

| | A Phase I, open-label, dose escalation study of oral LGK974 and PDR001 in patients with malignancies dependent on Wnt Ligands |
|---|---|
| | Tumor evaluations will also be performed at EOT for both portions of the study. If the last prior tumor evaluation was within 28 days of EOT, then it does not need to be repeated at EOT. Tumor evaluations after the baseline assessment will include evaluation of all sites of disease identified at baseline, using the same technique that was used at baseline. If there was no evidence of disease in a body region at baseline, that region does not need to be imaged at subsequent assessments, unless there is clinical concern for a new lesion in that body region. For the Compound of Formula (I) in combination with PDR001, the local investigator's assessment will be used for the analysis of response according to both RECIST 1.1 and irRC, and for treatment decision making (study discontinuation due to PD as per irRC). Patients experiencing progressive disease per RECIST v. 1.1 criteria may continue to be treated according to irRC guidelines until progression is documented via irRC. During the course of the study, the study sponsor may decide to have a central review of the radiological assessments performed. In such case, the investigator's staff will be instructed on how to send data from these radiological assessments to a Contract Research Organization (CRO) for central review when needed. |
| Safety assessments | Safety will be monitored by assessing changes from baseline in laboratory values, physical examination, and vital signs as well as collecting of the adverse events at every visit. Evaluation of all AEs and SAEs including injection site hypersensitivity reactions, vital signs, laboratory assessments and occurrence of infections. Physical examination Vital signs Height and weight Laboratory evaluations Hematology Clinical chemistry Bone-related laboratory assessments Urinalysis Pregnancy and assessments of fertility Thyroid function panel Cytokines Cardiac assessments Bone density scans Lumbar x-rays Pharmacokinetics and immunogenicity (IG) assessments |
| Data analysis | Data will be summarized using descriptive statistics (continuous data) and/or contingency tables (categorical data) for demographic and baseline characteristics, efficacy measurements, safety measurements, and all relevant pharmacokinetic and pharmacodynamic measurements. The primary CSR will be based on all patient data from the escalation and expansion parts up to the time when all patients have completed at least four cycles of treatment or discontinued the study. Any additional data for patients continuing to receive study treatment past the cutoff date of the primary CSR, as allowed by protocol, will be reported once all patients have completed SEC follow-up visit. Within this analysis, cohorts of patients treated at the same dose or combination, regimen, and formulation will be pooled into treatment groups. Also, within the combination portion of the study, patients treated during the escalation part will be pooled with those receiving the same dosing regimen during the expansion part. All listings, summaries, figures, and analyses will be performed by treatment group unless otherwise specified. Within the dose expansion part, additional descriptive analyses by indication group and route of administration may be performed if appropriate. |

Figure 8:
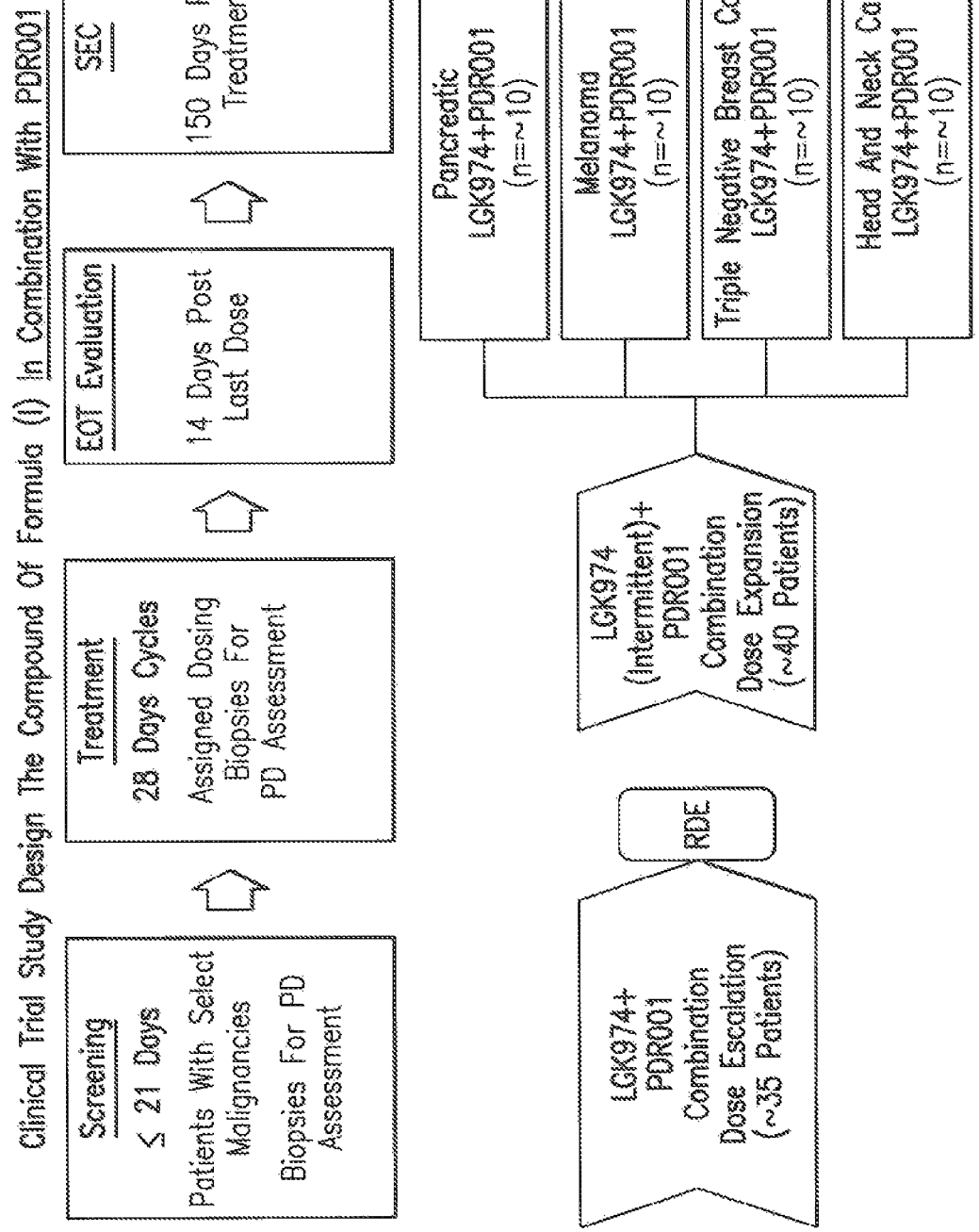
FIG. 8: illustrates the clinical study design.

The clinical trial design is shown in FIG. 8.

Example 3: Suppression of Pancreatic Growth Alone and in Combination with Immunotherapy The following experimental study will be used to confirm the rationale, findings, and conclusions of Example 1. The efficacy expected from Example 1 will also be further evaluated.

The study will examine the ability of the Compound of Formula (I), either alone or in combination with an anti-PD1 molecule to suppress the growth of pancreatic tumor cells in PDX-CRE KRAS$^{G12D}$ P53$^{R172H/+}$ mice.

Treatment groups:
A) Vehicle
B) Compound of Formula (I), 5 mg/kg BID, PO
C) Compound of Formula (I), 5 mg/kg BID, PO and anti-PD1 (twice weekly ip)
D) Compound of Formula (I), 5 mg/kg BID, PO and isotype control (twice weekly ip)
 Approximately 10-15 mice will be in each treatment group Treatment period: Treatment will begin when the mice have palpable tumor burden. Mice will be harvested when exhibiting symptoms of pancreatic cancer (median 120 days). Cohorts of treatment and control animals will be sample following short term treatment (less than 7 days) for analysis of tumour immune and inflammatory infiltrate.

Tumor growth will be monitored via ultrasound. Time to symptoms of pancreatic cancers and metastatic spread will also be monitored. HC for markers of differentiation, apoptosis, proliferation and senescence will be monitored, as well.

Readouts: IHC for nuclear β-catenin, BrdU incorporation, CD4+, CD8+, CD3+(T-lymphosycets), F4/8-(macrophage) and NIMP (neutrophils). Material and dta in the form of isolated RNA for cohort animals and whole transciptome analysis by RNASeq in combination with GSEA for immune and inflammatory signatures following short term intervention will be determined.

Example 4: Suppression of Melanoma Growth Alone and in Combination with Immunotherapy The following experimental study will be used to confirm the rationale, findings, and conclusions of Example 1. The efficacy expected from Example 1 will also be further evaluated.

The study will examine the ability of the Compound of Formula (I), either alone or in combination with an anti-PD1 molecule to suppress the growth of melanoma tumor cells in TyrCreER BRaf$^{V600E/+}$ Pten$^{fl/+}$ and TyrCreER BRaf$^{V600E/+}$ Pten$^{fl/+}$ Catnb$^{lox(ex3)/+}$ mice.

Treatment Groups:
A) Vehicle
B) Compound of Formula (I), 5 mg/kg BID, PO
C) Compound of Formula (I), 5 mg/kg BID, PO and anti-PD1 (twice weekly ip)
D) Compound of Formula (I), 5 mg/kg BID, PO and isotype control (twice weekly ip)
    Approximately 10-15 mice will be in each treatment group Treatment period: Treatment will begin upon establishment of melanoma (5 mm diameter) and continue until tumors reach endpoint (15 mm diameter). Tumor growth will be monitored by caliper measurement.

Readouts: Tumor growth by caliper measurement, tumor cellularity by pathological examination, IHC for β-catenin and qPCR for Wnt target genes, stromal cell/infiltrating immune cell markers by IHC.

Example 5: Suppression of Melanoma Growth Alone and in Combination with Immunotherapy The following experimental study will be used to confirm the rationale, findings, and conclusions of Example 1. The efficacy expected from Example 1 will also be further evaluated.

The study will examine the ability of the Compound of Formula (I), either alone or in combination with an anti-PD1 molecule to suppress the growth of melanoma tumor cells in CD-1 nude or C57BL/˄ mice grafted with mouse derived melanoma (TyrCreER BRaf$^{V600E/+}$ Pten$^{fl/+}$ and TyrCreER BRaf$^{V600E/+}$ Pten$^{fl/+}$ Catnb$^{lox(ex3)/+}$ mice.

Treatment Groups:
A) Vehicle
B) Compound of Formula (I), 5 mg/kg BID, PO
C) Compound of Formula (I), 5 mg/kg BID, PO and anti-PD1 (twice weekly ip)
D) Compound of Formula (I), 5 mg/kg BID, PO and isotype control (twice weekly ip)
    Approximately 10-15 mice will be in each treatment group Treatment period: Treatment will begin upon establishment of melanoma (5 mm diameter) and continue until tumors reach endpoint (15 mm diameter). Tumor growth will be monitored by caliper measurement.

Readouts: Tumor growth by caliper measurement, tumor cellularity by pathological examination, IHC for β-catenin and qPCR for Wnt target genes, stromal cell/infiltrating immune cell markers by IHC.

---

The invention claimed is:

1. A method of treating cancer comprising the administration of a pharmaceutical combination comprising (i) 2-(2',3-dimethyl-[2,4'-bipyridin]-5-yl)-N-(5-(pyrazin-2-yl)pyridin-2-yl)acetamide, or a pharmaceutically acceptable salt thereof, and (ii) anti-PD-1 antibody molecule or a pharmaceutically acceptable salt thereof, wherein (a) (i) is administered daily on days 1 to 15, or days 1 to 16, of each cycle for up to 4 cycles, or (b) (i) is administered daily during days 1 to 8 of each cycle for up to 4 cycles, (ii) is administered at least once per cycle, and wherein each cycle is 28 days or 30 days.

2. The method of treating cancer according to claim 1, wherein (i) is administered during the first cycle only or wherein (i) is administered during 4 cycles only.

3. The method of treating cancer according to claim 1, wherein each cycle is 28 days.

4. The method of treating cancer according to claim 1, wherein (i) is administered twice daily.

5. The method of treating cancer according to claim 4, wherein (i) is administered at 12-hour intervals.

6. The method of treating cancer according to claim 1, wherein the daily dose of (i) is 2.5 mg/day, 5 mg/day, 7.5 mg/day, 10 mg/day, 20 mg/day, 40 mg/day, 80 mg/day, 120 mg/day, or 180 mg/day.

7. The method of treating cancer according to claim 6, wherein the daily dose of (i) is 2.5 mg/day, 5 mg/day, or 10 mg/day.

8. The method of treating cancer according to claim 7, wherein the daily dose of (i) is 10 mg/day.

9. The method of treating cancer according to claim 1, wherein (ii) is administered every 2 weeks or every 4 weeks in a cycle.

10. The method of treating cancer according to claim 9, wherein (ii) is administered, every 4 weeks.

11. The method of treating cancer according to claim 1, wherein (ii) is PDR-001, or a pharmaceutical salt thereof.

12. The method of treating cancer according to claim 11, wherein (ii) is administered intravenously in a single dose of 300 to 400 mg/day.

13. The method of treating cancer according to claim 12, wherein the single dose is 400 mg/day.

14. The method of treating cancer according to claim 1, wherein (a) 2.5 mg/day of (i) is administered on days 1-8 or (b) 2.5 mg/day of (i) is administered on days 1-15; and 400 mg/day of (ii) is administered once every 4 weeks for up to 4 cycles.

15. The method of treating cancer according to claim 14, wherein 2.5 mg/day of (i) is administered during cycle 1 only and 400 mg/day of (ii) is administered every 4 weeks.

16. The method of treating cancer according to claim 1, wherein (a) 5 mg/day of (i) is administered on days 1-8, or (b) 5 mg/day of (i) is administered on days 1-15; and 400 mg/day of (ii) is administered once every 4 weeks for up to 4 cycles.

17. The method of treating cancer according to claim 16, wherein 5 mg/day of (i) is administered during cycle 1 only and 400 mg/day of (ii) is administered every 4 weeks.

18. The method of treating cancer according to claim 1, wherein (a) 10 mg/day of (i) is administered daily on days 1-8 or (b) 10 mg/day of (i) is administered on days 1-15; and 400 mg/day of (ii) is administered every 4 weeks for up to 4 cycles.

19. The method of treating cancer according to claim 18, wherein 10 mg/day of (i) is administered during cycle 1 only and 400 mg/day of (ii) is administered every 4 weeks.

20. The method of treating cancer according to claim 1, wherein (ii) is administered continuously every 4 weeks.

21. The method for the treatment of cancer according to claim 1 wherein the cancer is triple-negative breast cancer (TNBC), head and neck squamous cell carcinoma, pancreatic cancer, gastrointestinal cancer, colorectal cancer, squamous cell cancer of the lung, squamous cell cancer of the esophagus, squamous cell cancer of the cervix or melanoma.

22. The method for the treatment of cancer according to claim 21, wherein the cancer is triple-negative breast cancer (TNBC), pancreatic cancer or melanoma.

23. The method for the treatment of cancer according to claim 1, wherein (i) and (ii) are synergistically active at reducing bone resorption.

24. The method for the treatment of cancer according to claim 1, wherein (i) 2-(2',3-dimethyl-[2,4'-bipyridin]-5-yl)-N-(5-(pyrazin-2-yl)pyridin-2-yl)acetamide, or a pharmaceutically acceptable salt thereof, is administered orally or intravenously.

* * * * *

SEQUENCE LISTING

```
<160> NUMBER OF SEQ ID NOS: 224

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Thr Tyr Trp Met His
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Asn Ile Tyr Pro Gly Thr Gly Gly Ser Asn Phe Asp Glu Lys Phe Lys
1               5                   10                  15
```

Asn

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Trp Thr Thr Gly Thr Gly Ala Tyr
1               5

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Thr Phe Thr Thr Tyr
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Pro Gly Thr Gly Gly
1               5

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 17

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Ser Ser Gln Ser Leu Leu Asp Ser Gly Asn Gln Lys Asn Phe Leu
1               5                   10                  15

Thr

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Trp Ala Ser Thr Arg Glu Ser
1               5

<210> SEQ ID NO 12

<400> SEQUENCE: 12

000

<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gln Ser Leu Leu Asp Ser Gly Asn Gln Lys Asn Phe
1               5                   10

<210> SEQ ID NO 14
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Trp Ala Ser
1

<210> SEQ ID NO 15

<400> SEQUENCE: 15

000

<210> SEQ ID NO 16

<400> SEQUENCE: 16

000
```

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

```
<210> SEQ ID NO 28
<400> SEQUENCE: 28

000

<210> SEQ ID NO 29
<400> SEQUENCE: 29

000

<210> SEQ ID NO 30
<400> SEQUENCE: 30

000

<210> SEQ ID NO 31
<400> SEQUENCE: 31

000

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Asn Asp Tyr Ser Tyr Pro Tyr Thr
1               5

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Asp Tyr Ser Tyr Pro Tyr
1               5

<210> SEQ ID NO 34
<400> SEQUENCE: 34

000

<210> SEQ ID NO 35
<400> SEQUENCE: 35

000

<210> SEQ ID NO 36
<400> SEQUENCE: 36

000
```

```
<210> SEQ ID NO 37
<400> SEQUENCE: 37
000

<210> SEQ ID NO 38
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38
```

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

```
<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
```

```
<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54
```

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
                100                 105                 110

Lys
```

<210> SEQ ID NO 55

<400> SEQUENCE: 55

000

<210> SEQ ID NO 56
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190
```

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

```
<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 71

<400> SEQUENCE: 71

000

<210> SEQ ID NO 72
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
```

```
            35                  40                  45
Ala Pro Arg Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Phe Thr
 65                  70                  75                  80

Ile Ser Ser Leu Glu Ala Glu Asp Ala Ala Thr Tyr Tyr Cys Gln Asn
                 85                  90                  95

Asp Tyr Ser Tyr Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
210                 215                 220
```

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

```
<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90
```

000

```
<210> SEQ ID NO 91
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 91

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln

```
               340             345             350
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 92
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
gaagtgcagc tggtgcagtc tggcgccgaa gtgaagaagc tggcgagtc cctgcggatc      60
tcctgcaagg gctctggcta caccttcacc acctactgga tgcactgggt gcgacaggct    120
accggccagg gctggaatg gatgggcaac atctatcctg gcaccggcgg ctccaacttc     180
gacgagaagt tcaagaacag agtgaccatc accgccgaca gtccacctc caccgcctac    240
atggaactgt cctccctgag atccgaggac accgccgtgt actactgcac cggtggaca     300
accggcacag gcgcttattg gggccagggc accacagtga ccgtgtcctc tgcttctacc    360
aagggcccca gcgtgttccc cctggcccc tgctccagaa gcaccagcga gagcacagcc    420
gccctgggct gcctggtgaa ggactacttc cccgagcccg tgaccgtgtc ctggaacagc    480
ggagccctga ccagcggcgt gcacaccttc ccgccgtgc tgcagagcag cggcctgtac    540
agcctgagca gcgtggtgac cgtgcccagc agcagcctgg gcaccaagac ctacacctgt    600
aacgtggacc acaagcccag caacaccaag gtggacaaga gggtggagag caagtacggc    660
ccaccctgcc cccctgccc agcccccgag ttcctgggcg acccagcgt gttcctgttc       720
cccccaagc caaggacac cctgatgatc agcagaaccc ccgaggtgac ctgtgtggtg      780
gtggacgtgt cccaggagga cccgaggtc cagttcaact ggtacgtgga cggcgtggag     840
gtgcacaacg ccaagaccaa gcccagagag gagcagtttta acagcaccta ccgggtggtg    900
tccgtgctga ccgtgctgca ccaggactgg ctgaacggca agagtacaa gtgtaaggtc      960
tccaacaagg cctgccaag cagcatcgaa aagaccatca gcaaggccaa gggccagcct     1020
agagagcccc aggtctacac cctgccaccc agccaagagg agatgaccaa gaaccaggtg   1080
tccctgacct gtctggtgaa gggcttctac ccaagcgaca tcgccgtgga gtgggagagc   1140
aacggccagc ccgagaacaa ctacaagacc acccccccag tgctggacag cgacggcagc    1200
ttcttcctgt acagcaggct gaccgtggac aagtccagat ggcaggaggg caacgtcttt    1260
agctgctccg tgatgcacga ggccctgcac aaccactaca cccagaagag cctgagcctg    1320
tccctgggc                                                            1329
```

<210> SEQ ID NO 93

<400> SEQUENCE: 93

000

<210> SEQ ID NO 94

<400> SEQUENCE: 94

000

<210> SEQ ID NO 95
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

```
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag c              351
```

<210> SEQ ID NO 96
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96

```
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag cgctagcact     360
aagggcccgt ccgtgttccc cctggcacct tgtagccgga gcactagcga atccaccgct     420
gccctcggct gcctggtcaa ggattacttc ccggagcccg tgaccgtgtc ctggaacagc     480
ggagccctga cctccggagt gcacaccttc ccgctgtgc tgcagagctc cgggctgtac     540
tcgctgtcgt cggtggtcac ggtgccttca tctagcctgg gtaccaagac ctacacttgc     600
aacgtggacc acaagccttc caacactaag gtggacaagc gcgtcgaatc gaagtacggc     660
ccaccgtgcc cgccttgtcc cgcgccggag ttcctcggcg gtccctcggt ctttctgttc     720
ccaccgaagc ccaaggacac tttgatgatt tcccgcaccc ctgaagtgac atgcgtggtc     780
gtggacgtgt cacaggaaga tccggaggtg cagttcaatt ggtacgtgga tggcgtcgag     840
gtgcacaacg ccaaaaccaa gccgagggag gagcagttca actccactta ccgcgtcgtg     900
```

```
tccgtgctga cggtgctgca tcaggactgg ctgaacggga aggagtacaa gtgcaaagtg      960
tccaacaagg gacttcctag ctcaatcgaa aagaccatct cgaaagccaa gggacagccc     1020
cgggaacccc aagtgtatac cctgccaccg agccaggaag aaatgactaa gaaccaagtc     1080
tcattgactt gccttgtgaa gggcttctac ccatcggata tcgccgtgga atgggagtcc     1140
aacggccagc cggaaaacaa ctacaagacc acccctccgg tgctggactc agacggatcc     1200
ttcttcctct actcgcggct gaccgtggat aagagcagat ggcaggaggg aaatgtgttc     1260
agctgttctg tgatgcatga agccctgcac aaccactaca ctcagaagtc cctgtccctc     1320
tccctggga                                                             1329
```

<210> SEQ ID NO 97
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97

```
gagatcgtcc tgactcagtc acccgctacc ctgagcctga gcctggcga gcgggctaca       60 ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300
ccctacacct tcggtcaagg cactaaggtc gagattaag                            339
```

<210> SEQ ID NO 98
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98

```
gagatcgtcc tgactcagtc acccgctacc ctgagcctga gcctggcga gcgggctaca       60 ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300
ccctacacct tcggtcaagg cactaaggtc gagattaagc gtacggtggc cgctcccagc     360
gtgttcatct ccccccccag cgacgagcag ctgaagagcg gcaccgccag cgtggtgtgc     420
ctgctgaaca cttctacccc ccgggaggcc aaggtgcagt ggaaggtgga caacgccctg     480
cagagcggca acagccagga gagcgtcacc gagcaggaca gcaaggactc cacctacagc     540
ctgagcagca ccctgaccct gagcaaggcc gactacgaga gcataaaggt gtacgcctgc     600
gaggtgaccc accagggcct gtccagcccc gtgaccaaga gcttcaacag gggcgagtgc     660
```

<210> SEQ ID NO 99

<400> SEQUENCE: 99

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

```
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg tcaagcccct agactgctga tctactgggc ctctactaga     180
gaatcaggcg tgccctctag gtttagcggt agcggtagtg gcaccgactt caccttcact     240
atctctagcc tggaagccga ggacgccgct acctactact gtcagaacga ctatagctac     300
ccctacacct tcggtcaagg cactaaggtc gagattaag                            339
```

<210> SEQ ID NO 107
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 107

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg tcaagcccct agactgctga tctactgggc ctctactaga   180
gaatcaggcg tgccctctag gtttagcggt agcggtagtg gcaccgactt caccttcact   240
atctctagcc tggaagccga ggacgccgct acctactact gtcagaacga ctatagctac   300
ccctacacct tcggtcaagg cactaaggtc gagattaagc gtacggtggc cgctcccagc   360
gtgttcatct ccccccccag cgacgagcag ctgaagagcg gcaccgccag cgtggtgtgc   420
ctgctgaaca acttctaccc ccgggaggcc aaggtgcagt ggaaggtgga caacgccctg   480
cagagcggca acagccagga gagcgtcacc gagcaggaca gcaaggactc cacctacagc   540
ctgagcagca ccctgaccct gagcaaggcc gactacgaga agcataaggt gtacgcctgc   600
gaggtgaccc accagggcct gtccagcccc gtgaccaaga gcttcaacag gggcgagtgc   660
```

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
<400> SEQUENCE: 126
000

<210> SEQ ID NO 127

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
acctactgga tgcac                                                      15

<210> SEQ ID NO 134
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
aatatctacc ccggcaccgg cggctctaac ttcgacgaga agtttaagaa t               51

<210> SEQ ID NO 135
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135

```
tggactaccg gcacaggcgc ctac                                           24
```

<210> SEQ ID NO 136
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136

```
ggctacacct tcactaccta c                                              21
```

<210> SEQ ID NO 137
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137

```
taccccggca ccggcggc                                                  18
```

<210> SEQ ID NO 138
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138

```
aaatctagtc agtcactgct ggatagcggt aatcagaaga acttcctgac c              51
```

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139

```
tgggcctcta ctagagaatc a                                              21
```

<210> SEQ ID NO 140
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140

```
cagaacgact atagctaccc ctacacc                                        27
```

<210> SEQ ID NO 141
<211> LENGTH: 39
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 141
agtcagtcac tgctggatag cggtaatcag aagaacttc                          39

<210> SEQ ID NO 142
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142 tgggcctct                                                           9

<210> SEQ ID NO 143
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gactatagct acccctac                                                 18

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 148
<211> LENGTH: 75
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gaagtgcagc tggtgcagtc tggagcagag gtgaaaaagc ccggggagtc tctgaggatc    60
tcctgtaagg gttct                                                     75

<210> SEQ ID NO 149
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
gaagtgcagc tggtgcagtc tggcgccgaa gtgaagaagc ctggcgagtc cctgcggatc    60
tcctgcaagg gctct                                                     75

<210> SEQ ID NO 150
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
gaggtgcagc tggtgcagtc aggcgccgaa gtgaagaagc ccggcgagtc actgagaatt    60
agctgtaaag gttca                                                     75

<210> SEQ ID NO 151
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 152
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
caggttcagc tggtgcagtc tggagctgag gtgaagaagc tgggggcctc agtgaaggtc    60
tcctgcaagg cttct                                                     75

```
<210> SEQ ID NO 153
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Trp Val Arg Gln Ala Thr Gly Gln Gly Leu Glu Trp Met Gly
1               5                   10

<210> SEQ ID NO 154
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
tgggtgcgac aggccactgg acaagggctt gagtggatgg gt                    42

<210> SEQ ID NO 155
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
tgggtgcgac aggctaccgg ccagggcctg gaatggatgg gc                    42

<210> SEQ ID NO 156
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
tgggtccgcc aggctaccgg tcaaggcctc gagtggatgg gt                    42

<210> SEQ ID NO 157
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Trp Ile Arg Gln Ser Pro Ser Arg Gly Leu Glu Trp Leu Gly
1               5                   10

<210> SEQ ID NO 158
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 158
tggatcaggc agtccccatc gagaggcctt gagtggctgg gt          42

<210> SEQ ID NO 159
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
tggatccggc agtcccccte tagggggcctg gaatggctgg gc          42

<210> SEQ ID NO 160
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Trp Val Arg Gln Ala Pro Gly Gln Gly Leu Glu Trp Met Gly
1               5                   10

<210> SEQ ID NO 161
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
tgggtgcgac aggcccctgg acaagggctt gagtggatgg gt          42

<210> SEQ ID NO 162
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 163
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
agagtcacga ttaccgcgga caaatccacg agcacagcct acatggagct gagcagcctg  60
agatctgagg acacggccgt gtattactgt acaaga  96

<210> SEQ ID NO 164
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
agagtgacca tcaccgccga caagtccacc tccaccgcct acatggaact gtcctccctg  60
agatccgagg acaccgccgt gtactactgc acccgg  96

<210> SEQ ID NO 165
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
agagtgacta tcaccgccga taagtctact agcaccgcct atatggaact gtctagcctg  60
agatcagagg acaccgccgt ctactactgc actagg  96

<210> SEQ ID NO 166
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 167
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
agattcacca tctccagaga caattccaag aacacgctgt atcttcaaat gaacagcctg  60
agagccgagg acacggccgt gtattactgt acaaga  96

<210> SEQ ID NO 168
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<400> SEQUENCE: 168
aggttcacca tctcccggga caactccaag aacaccctgt acctgcagat gaactccctg    60
cgggccgagg acaccgccgt gtactactgt accaga                              96

<210> SEQ ID NO 169
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Trp Gly Gln Gly Thr Thr Val Thr Val Ser Ser
1               5                   10

<210> SEQ ID NO 170
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
tggggccagg gcaccaccgt gaccgtgtcc tcc                                  33

<210> SEQ ID NO 171
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
tggggccagg gcaccacagt gaccgtgtcc tct                                  33

<210> SEQ ID NO 172
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
tggggtcaag gcactaccgt gaccgtgtct agc                                  33

<210> SEQ ID NO 173
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
tggggccagg gcacaacagt gaccgtgtcc tcc                                  33
```

<210> SEQ ID NO 174
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 174

Glu Ile Val Leu Thr Gln Ser Pro Asp Phe Gln Ser Val Thr Pro Lys
1               5                   10                  15
Glu Lys Val Thr Ile Thr Cys
            20

<210> SEQ ID NO 175
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 175
gaaattgtgc tgactcagtc tccagacttt cagtctgtga ctccaaagga gaaagtcacc      60
atcacctgc                                                             69

<210> SEQ ID NO 176
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
gagatcgtgc tgacccagtc ccccgacttc cagtccgtga cccccaaaga aaaagtgacc      60
atcacatgc                                                             69

<210> SEQ ID NO 177
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 177

Glu Ile Val Leu Thr Gln Ser Pro Ala Thr Leu Ser Leu Ser Pro Gly
1               5                   10                  15
Glu Arg Ala Thr Leu Ser Cys
            20

<210> SEQ ID NO 178
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178

```
gaaattgtgt tgacacagtc tccagccacc ctgtctttgt ctccagggga aagagccacc    60
ctctcctgc                                                            69
```

<210> SEQ ID NO 179
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179

```
gagatcgtgc tgacccagtc ccctgccacc ctgtcactgt ctccaggcga gagagctacc    60
ctgtcctgc                                                            69
```

<210> SEQ ID NO 180
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180

```
gagatcgtcc tgactcagtc acccgctacc ctgagcctga gccctggcga gcgggctaca    60
ctgagctgt                                                            69
```

<210> SEQ ID NO 181
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

```
Asp Ile Val Met Thr Gln Thr Pro Leu Ser Leu Pro Val Thr Pro Gly
1               5                   10                  15

Glu Pro Ala Ser Ile Ser Cys
            20
```

<210> SEQ ID NO 182
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182

```
gatattgtga tgacccagac tccactctcc ctgcccgtca cccctggaga gccggcctcc    60
atctcctgc                                                            69
```

<210> SEQ ID NO 183
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 184
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gatgttgtga tgactcagtc tccactctcc ctgcccgtca cccttggaca gccggcctcc      60
atctcctgc                                                             69

<210> SEQ ID NO 185
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 186
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gacatccaga tgacccagtc tccatcctcc ctgtctgcat ctgtaggaga cagagtcacc      60
atcacttgc                                                             69

<210> SEQ ID NO 187
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Trp Tyr Gln Gln Lys Pro Gly Gln Ala Pro Arg Leu Leu Ile Tyr
1               5                   10                  15

<210> SEQ ID NO 188
<211> LENGTH: 45
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 188
tggtaccagc agaaacctgg ccaggctccc aggctcctca tctat              45

<210> SEQ ID NO 189
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
tggtatcagc agaagcccgg ccaggccccc agactgctga tctac              45

<210> SEQ ID NO 190
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
tggtatcagc agaagcccgg tcaagcccct agactgctga tctac              45

<210> SEQ ID NO 191
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Trp Tyr Gln Gln Lys Pro Gly Lys Ala Pro Lys Leu Leu Ile Tyr
1               5                   10                  15

<210> SEQ ID NO 192
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
tggtatcagc agaaaccagg gaaagctcct aagctcctga tctat              45

<210> SEQ ID NO 193
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
tggtatcagc agaagcccgg taaagcccct aagctgctga tctac              45
```

<210> SEQ ID NO 194
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 194

Trp Tyr Leu Gln Lys Pro Gly Gln Ser Pro Gln Leu Leu Ile Tyr
1               5                   10                  15

<210> SEQ ID NO 195
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195
tggtacctgc agaagccagg gcagtctcca cagctcctga tctat          45

<210> SEQ ID NO 196
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 196

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
                20                  25                  30

<210> SEQ ID NO 197
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
ggggtcccct cgaggttcag tggcagtgga tctgggacag atttcacctt taccatcagt    60
agcctggaag ctgaagatgc tgcaacatat tactgt                              96

<210> SEQ ID NO 198
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
ggcgtgccct ctagattctc cggctccggc tctggcaccg actttacctt caccatctcc    60
agcctggaag ccgaggacgc cgccacctac tactgc                              96

<210> SEQ ID NO 199
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ggcgtgccct ctaggtttag cggtagcggt agtggcaccg acttcacctt cactatctct    60
agcctggaag ccgaggacgc cgctacctac tactgt                              96

<210> SEQ ID NO 200
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 201
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
gggatcccac ctcgattcag tggcagcggg tatggaacag attttaccct cacaattaat    60
aacatagaat ctgaggatgc tgcatattac ttctgt                              96

<210> SEQ ID NO 202
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 203
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 203
ggggtcccat caaggttcag cggcagtgga tctgggacag aattcactct caccatcagc    60
agcctgcagc ctgatgattt tgcaacttat tactgt    96

<210> SEQ ID NO 204
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
ggcgtgccct ctagattctc cggctccggc tctggcaccg agtttaccct gaccatctcc    60
agcctgcagc ccgacgactt cgccacctac tactgc    96

<210> SEQ ID NO 205
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 206
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
ggggtcccat caaggttcag tggaagtgga tctgggacag attttacttt caccatcagc    60
agcctgcagc ctgaagatat tgcaacatat tactgt    96

<210> SEQ ID NO 207
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
ggcgtgccct ctaggtttag cggtagcggt agtggcaccg acttcacctt cactatctct    60
agcctgcagc ccgaggatat cgctacctac tactgt    96

<210> SEQ ID NO 208
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Phe Gly Gln Gly Thr Lys Val Glu Ile Lys
1               5                   10

<210> SEQ ID NO 209
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ttcggccaag ggaccaaggt ggaaatcaaa                                    30

<210> SEQ ID NO 210
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ttcggccagg gcaccaaggt ggaaatcaag                                    30

<210> SEQ ID NO 211
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ttcggtcaag gcactaaggt cgagattaag                                    30

<210> SEQ ID NO 212
<211> LENGTH: 327
<212> TYPE: PRT
<213> ORGANISM: Homo sapiens

<400> SEQUENCE: 212

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 213
<211> LENGTH: 107
<212> TYPE: PRT
<213> ORGANISM: Homo sapiens

<400> SEQUENCE: 213

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 214
<211> LENGTH: 326
<212> TYPE: PRT
<213> ORGANISM: Homo sapiens

<400> SEQUENCE: 214
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 215
<211> LENGTH: 330
<212> TYPE: PRT
<213> ORGANISM: Homo sapiens

<400> SEQUENCE: 215

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 216
<211> LENGTH: 330
<212> TYPE: PRT
<213> ORGANISM: Homo sapiens

<400> SEQUENCE: 216

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
                     85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 217
<211> LENGTH: 330
<212> TYPE: PRT
<213> ORGANISM: Homo sapiens

<400> SEQUENCE: 217

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
            130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 218
<211> LENGTH: 330
<212> TYPE: PRT
<213> ORGANISM: Homo sapiens

<400> SEQUENCE: 218

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 219

<400> SEQUENCE: 219

000

<210> SEQ ID NO 220

<400> SEQUENCE: 220

000

<210> SEQ ID NO 221
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Met Ala Trp Val Trp Thr Leu Pro Phe Leu Met Ala Ala Ala Gln Ser
1               5                   10                  15

Val Gln Ala

<210> SEQ ID NO 222
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Met Ser Val Leu Thr Gln Val Leu Ala Leu Leu Leu Leu Trp Leu Thr
1               5                   10                  15

Gly Thr Arg Cys
            20

```
<210> SEQ ID NO 223

<400> SEQUENCE: 223

000

<210> SEQ ID NO 224
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Gly Tyr Thr Phe Thr Thr Tyr Trp Met His
1               5                   10
```